United States Patent
Kajimoto et al.

(10) Patent No.: US 11,672,171 B2
(45) Date of Patent: Jun. 6, 2023

(54) LIGHT-EMITTING DEVICE INCLUDING A PLURALITY OF ORGANIC ELECTROLUMINESCENT ELEMENTS

(71) Applicant: CANON KABUSHIKI KAISHA, Tokyo (JP)

(72) Inventors: Norifumi Kajimoto, Zama (JP); Tetsuo Takahashi, Kawasaki (JP); Koji Ishizuya, Kawasaki (JP); Itaru Takaya, Atsugi (JP); Hirokazu Miyashita, Ebina (JP); Takayuki Ito, Kawasaki (JP); Hiroaki Sano, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 59 days.

(21) Appl. No.: 17/202,020

(22) Filed: Mar. 15, 2021

(65) Prior Publication Data

US 2021/0202848 A1     Jul. 1, 2021

Related U.S. Application Data

(63) Continuation of application No. 16/162,203, filed on Oct. 16, 2018, now Pat. No. 10,985,323.

(30) Foreign Application Priority Data

Oct. 19, 2017   (JP) .............................. JP2017-202820
Sep. 3, 2018    (JP) .............................. JP2018-164460

(51) Int. Cl.
*H10K 85/60*     (2023.01)
*H10K 50/13*     (2023.01)
(Continued)

(52) U.S. Cl.
CPC .......... *H01L 51/006* (2013.01); *C07C 211/00* (2013.01); *C07C 211/01* (2013.01);
(Continued)

(58) Field of Classification Search
CPC . H01L 51/006; H01L 51/0061; H01L 51/504; H01L 51/5064; H01L 51/5088;
(Continued)

(56) References Cited

U.S. PATENT DOCUMENTS

2010/0164842 A1*  7/2010  Ishihara .............. H01L 51/5265
                                                                345/32

FOREIGN PATENT DOCUMENTS

CN      1362747 A     8/2002
CN      1898292 A     1/2007
(Continued)

*Primary Examiner* — Shahed Ahmed
*Assistant Examiner* — Vicki B. Booker
(74) *Attorney, Agent, or Firm* — Canon U.S.A., Inc IP Division

(57) ABSTRACT

A light-emitting device includes a plurality of organic EL elements. Each of the organic EL elements includes a reflection electrode, a hole transport region, an electron-trapping luminescent layer, and a light extraction electrode in this order. The hole transport region has a sheet resistance of $4.0\times10^7$ Ω/sq.• or more at a current of 0.1 nA/pixel, and the total thickness of the hole transport region and the electron-trapping luminescent layer is equivalent to an optical path length enabling emission from the electron-trapping luminescent layer to be enhanced.

15 Claims, 11 Drawing Sheets

(51) Int. Cl.
| | |
|---|---|
| H10K 50/17 | (2023.01) |
| H10K 50/818 | (2023.01) |
| H10K 50/18 | (2023.01) |
| H10K 50/82 | (2023.01) |
| H10K 50/852 | (2023.01) |
| H10K 50/15 | (2023.01) |
| H10K 59/30 | (2023.01) |
| H10K 39/32 | (2023.01) |
| C07C 211/01 | (2006.01) |
| C07C 211/43 | (2006.01) |
| C07C 211/00 | (2006.01) |
| C07C 211/33 | (2006.01) |
| H10K 59/38 | (2023.01) |
| H10K 50/16 | (2023.01) |
| H01L 27/146 | (2006.01) |
| H10K 102/00 | (2023.01) |
| H01L 51/00 | (2006.01) |
| H01L 51/50 | (2006.01) |
| H01L 51/52 | (2006.01) |
| H01L 27/32 | (2006.01) |
| H01L 27/30 | (2006.01) |

(52) U.S. Cl.
CPC .......... *C07C 211/33* (2013.01); *C07C 211/43* (2013.01); *H01L 27/307* (2013.01); *H01L 27/3206* (2013.01); *H01L 51/0061* (2013.01); *H01L 51/504* (2013.01); *H01L 51/5064* (2013.01); *H01L 51/5088* (2013.01); *H01L 51/5096* (2013.01); *H01L 51/5218* (2013.01); *H01L 51/5221* (2013.01); *H01L 51/5265* (2013.01); *H01L 27/14612* (2013.01); *H01L 27/322* (2013.01); *H01L 51/0054* (2013.01); *H01L 51/0055* (2013.01); *H01L 51/0056* (2013.01); *H01L 51/0058* (2013.01); *H01L 51/0059* (2013.01); *H01L 51/0072* (2013.01); *H01L 51/5056* (2013.01); *H01L 51/5072* (2013.01); *H01L 2251/5315* (2013.01); *H01L 2251/558* (2013.01)

(58) Field of Classification Search
CPC ............. H01L 51/5096; H01L 51/5218; H01L 51/5221; H01L 51/5265; H01L 51/0054; H01L 51/0055; H01L 51/0056; H01L 51/0058; H01L 51/0059; H01L 51/0072; H01L 51/5056; H01L 51/5072; H01L 27/307; H01L 27/3206; H01L 27/14612; H01L 27/322
See application file for complete search history.

(56) References Cited

FOREIGN PATENT DOCUMENTS

| | | |
|---|---|---|
| CN | 101931057 A | 12/2010 |
| JP | 2010147332 A | 7/2010 |

* cited by examiner

LIGHT-EMITTING DEVICE INCLUDING A PLURALITY OF ORGANIC ELECTROLUMINESCENT ELEMENTS

CROSS-REFERENCE TO RELATED APPLICATIONS

This application is a continuation, and claims the benefit, of U.S. patent application Ser. No. 16/162,203, filed on Oct. 16, 2018, and claims the benefit of Japanese Patent Application No. 2017-202820 filed Oct. 19, 2017 and No. 2018-164460 filed Sep. 3, 2018, which are hereby incorporated by reference herein in their entirety.

BACKGROUND

Field of the Disclosure

The present disclosure relates to a light-emitting device including a plurality of organic EL elements and to an image forming device, a display device, and an imaging apparatus.

Description of the Related Art

An organic electroluminescent element (hereinafter referred to as an organic EL element) includes a pair of electrodes and an organic compound layer between the pair of electrodes. In a known element, the pair of electrodes consist of a metal electrode including a metal reflection layer and a transparent electrode. Organic EL elements operable at a low voltage have recently attracted attention. Such organic EL elements have advantageous features including surface emission, low weight, and good visibility and are being used in practice as light-emitting devices in flat displays, lighting devices, head-mounted displays, and print head light sources of electrophotographic printers.

In particular, there is an increasing demand for high-definition organic EL display devices, and a type using white organic EL elements and color filters (hereinafter referred to as a white+CF type) is known. The white+CF type can be manufactured with a higher yield than a type using a very fine metal mask because the organic compound layer of the white+CF type is formed over the entire surface of the substrate by vapor deposition. Also, since the pixel size and the interval between the pixels are not restricted by the deposition precision of the organic compound layer, the definition of white+CF organic EL display devices is increased relatively easily.

However, when the organic compound layer is shared by all the organic EL elements, leakage of the driving current is likely to occur between any two adjacent organic EL elements. Consequently, the pixels that should not emit light are affected by the pixels that should emit light, thereby emitting a slight amount of unwanted light. This causes a decrease in color gamut and efficiency.

Japanese Patent Laid-Open No. 2012-216338 (hereinafter referred to as PTL 1) discloses that the thickness of the portion of the organic compound layer between the pixels is reduced by forming a groove in the insulating layer between the pixels. Since the resistance of the thinned portion of the organic compound layer is increased, leakage current is reduced.

Japanese Patent Laid-Open No. 2014-232631 (hereinafter referred to as PTL 2) discloses a structure having a discontinuous organic compound layer formed by reversely tapering the ends of insulating partitions between the pixels. The discontinuous organic compound layer reduces leakage current.

In the structures disclosed in PTL 1 and PTL 2, however, the steep form thereof may cause the sealing layer to be degraded or the upper electrode to be disconnected.

It is known that by reducing the thickness of the organic compound layer, the resistance is increased. However, when the reflection electrode and the luminescent layer are close to each other, optical interference does not occur effectively and, accordingly, the optical element requires high power consumption.

SUMMARY

Accordingly, the present disclosure provides a light-emitting device in which leakage current between neighboring organic EL elements is reduced and in which optical interference occurs effectively, thereby reducing the power consumption.

According to an aspect of the present disclosure, there is provided a light-emitting device including a plurality of organic EL elements. Each of the organic EL elements includes a reflection electrode, a hole transport region, an electron-trapping luminescent layer, and a light extraction electrode in this order. The hole transport region has a sheet resistance of $4.0 \times 10^7$ Ω/sq. or more at a current of 0.1 nA/pixel, and the total thickness of the hole transport region and the electron-trapping luminescent layer is equivalent to an optical path length enabling emission from the electron-trapping luminescent layer to be enhanced.

Further features of the present disclosure will become apparent from the following description of exemplary embodiments with reference to the attached drawings.

DESCRIPTION OF THE EMBODIMENTS

In the light-emitting device according to an embodiment of the present disclosure, leakage current between neighboring organic EL elements is reduced, and the power consumption of the light-emitting device is reduced. Each organic EL element includes a reflection electrode, a hole transport region, an electron-trapping luminescent layer, and a light extraction electrode. In the embodiments of the present disclosure, the sheet resistance per pixel in the in-plane direction of the hole transport region is $4.0 \times 10^7$ $\Omega$/sq. or more and, thus, the leakage current between organic EL elements is reduced. Also, the presence of the electron-trapping luminescent layer makes the distance between the reflection electrode and the emission point an optical path length that enables the emission from the luminescent layer to be enhanced.

Figure 1:
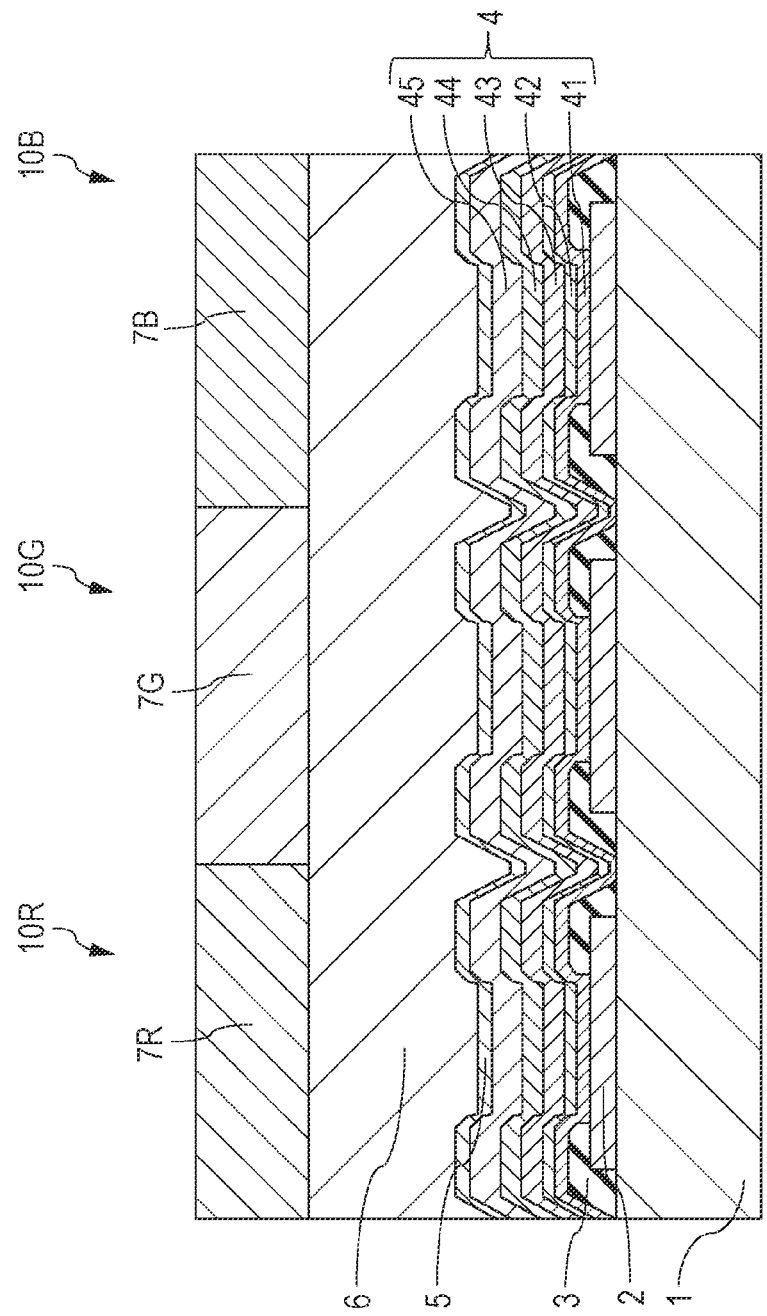
FIG. 1 is a schematic sectional view of a light-emitting device according to an embodiment of the present disclosure.

FIG. 1 is a schematic sectional view of a light-emitting device according to an embodiment of the present disclosure. The light-emitting device shown in FIG. 1 includes a substrate 1 and three types (R, G, and B) of organic EL elements 10R, 10G, and 10B, that are disposed on the substrate and that each include a reflection electrode 2, and an organic compound layer 4, a light extraction electrode 5, a sealing layer 6, and any one of color filters 7R, 7G, and 7B. The organic compound layer 4 and the light extraction electrode 5 are each disposed continuously in the in-plane direction along the main surface of the substrate 1. The three neighboring organic EL elements 10R, 10G, and 10B are separated from each other by an insulating layer 3. More specifically, the insulating layer 3 is disposed at the end of each reflection electrode 2 and disposed at upper surface of the end. The insulating layer 3 is intended to ensure insulation between any two adjacent reflection electrodes 2B, 2G, and 2R and insulation between each reflection electrode and the light extraction electrode 5 and to accurately define the light-emitting regions in a desired shape.

The organic compound layer 4 is a common layer shared by the plurality of organic EL elements. The term "common layer" implies that the layer is disposed across the plurality of organic EL elements and may be formed by a coating process, such as spin coating, or vapor deposition for the entire surface of the substrate. Fact that the organic compound layer 4 is a common layer implies that a plurality of reflection electrodes are provided on one organic compound layer.

In the present embodiment, the reflection electrode 2 is positive and the light extraction electrode 5 is negative.

In the present embodiment, the organic compound layer 4 includes a plurality of layers: a hole transport layer 41, an electron blocking layer 42, a first luminescent layer 43, a second luminescent layer 44, and an electron transport layer 45. The organic compound layer may include further organic compound layers. The organic compound layers disposed between the reflection electrode 2 and the first luminescent layer 43 are collectively referred to as a hole transport region. In another embodiment, the hole transport region may include a hole injection layer, a hole transport layer, and an electron blocking layer.

Each organic EL element is electrically connected to the adjacent organic EL elements by the hole transport region. In the light-emitting device of the present embodiment, the sheet resistance per pixel in the in-plane direction of the hole transport region is $4.0 \times 10^7$ $\Omega$/sq. or more at a current of 0.1 nA/pixel from the viewpoint of reducing leakage current between neighboring organic EL elements. More likely, the sheet resistance may be $6.0 \times 10^7$ $\Omega$/sq. or more.

Figure 2:
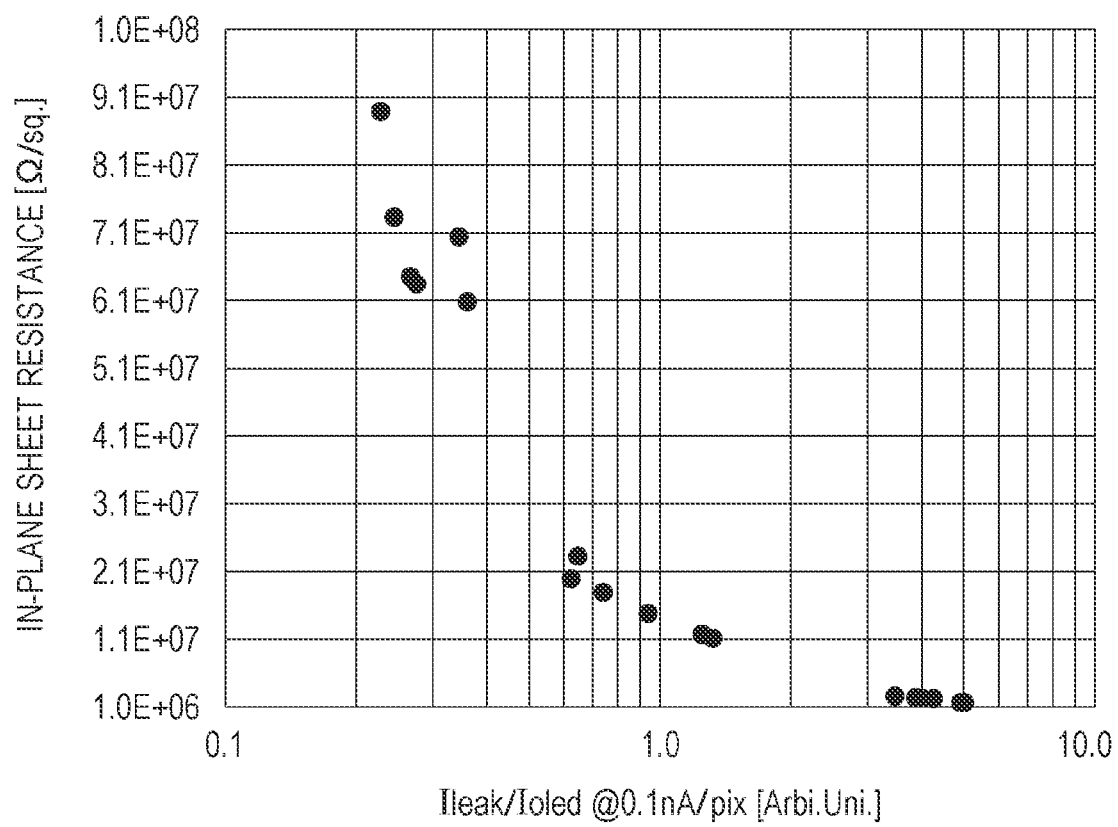
FIG. 2 is a plot showing the relationship between the sheet resistance of the hole transport region and the $I_{leak}/I_{oled}$ ratio of the leakage current $I_{leak}$ flowing from a target organic EL element to an adjacent organic EL element to the current $I_{oled}$ flowing into the target organic EL element.

FIG. 2 is a plot showing the relationship between the sheet resistance of the hole transport region and the $I_{leak}/I_{oled}$ ratio of the leakage current $I_{leak}$ flowing from a target organic EL element to an adjacent organic EL element to the current $I_{oled}$ flowing into the target organic EL element. Measurement of current $I_{oled}$ and leakage current $I_{leak}$ at a Red organic EL element (R pixel) will be described by way of example. The Red organic EL element is electrified in a state where the adjacent Green and Blue organic EL elements are short-circuited (potential: 0 V). At this time, the current flowing from the reflection electrode of the Red organic EL element to the light extraction electrode of the Red organic EL element is defined as $I_{oled}$, and the current flowing from the reflection electrode of the Red organic EL element to the reflection electrode of the Green organic EL element (G pixel) or the Blue organic EL element (B pixel) is defined as $I_{leak}$. The sheet resistance per pixel in the in-plane direction is calculated by using equation (1). In this instance, the sheet resistance is the value when current $I_{oled}$ is 0.1 nA/pixel.

$$Rs = dI_{leak}/dV * W/L \tag{1}$$

In this equation, W represents the total width of the two adjacent organic EL elements, L represents the distance between the two adjacent organic EL elements, and V represents the voltage applied to the target organic EL element. $dI_{leak}/dV$ represents the differential resistance.

The hole transport region includes a plurality of organic compound layers. The hole transport region may include a hole injection layer, a hole transport layer, and an electron blocking layer. These layers may be used independently or in combination. Each layer of the hole transport region may be composed of a single compound or may contain a plurality of compounds.

In an embodiment in which the hole transport region includes a hole transport layer, the thickness of the hole transport layer may be less than 10 nm. As the thickness of the hole transport layer is smaller, the thickness of the hole transport layer at the side wall of the insulating layer decreases. Accordingly, the resistance between the organic EL elements tends to increase. In some embodiments, the thickness of the hole transport layer may be 7 nm or less or 5 nm or less.

In view of the resistance in the in-plane direction, the hole mobility of the hole transport layer in the direction parallel to the main surface of the substrate is beneficially $2.5 \times 10^{-3}$ cm$^2$/(V·s) or less, for example, $1.0 \times 10^{-3}$ cm$^2$/(V·s) or less.

Figure 4:
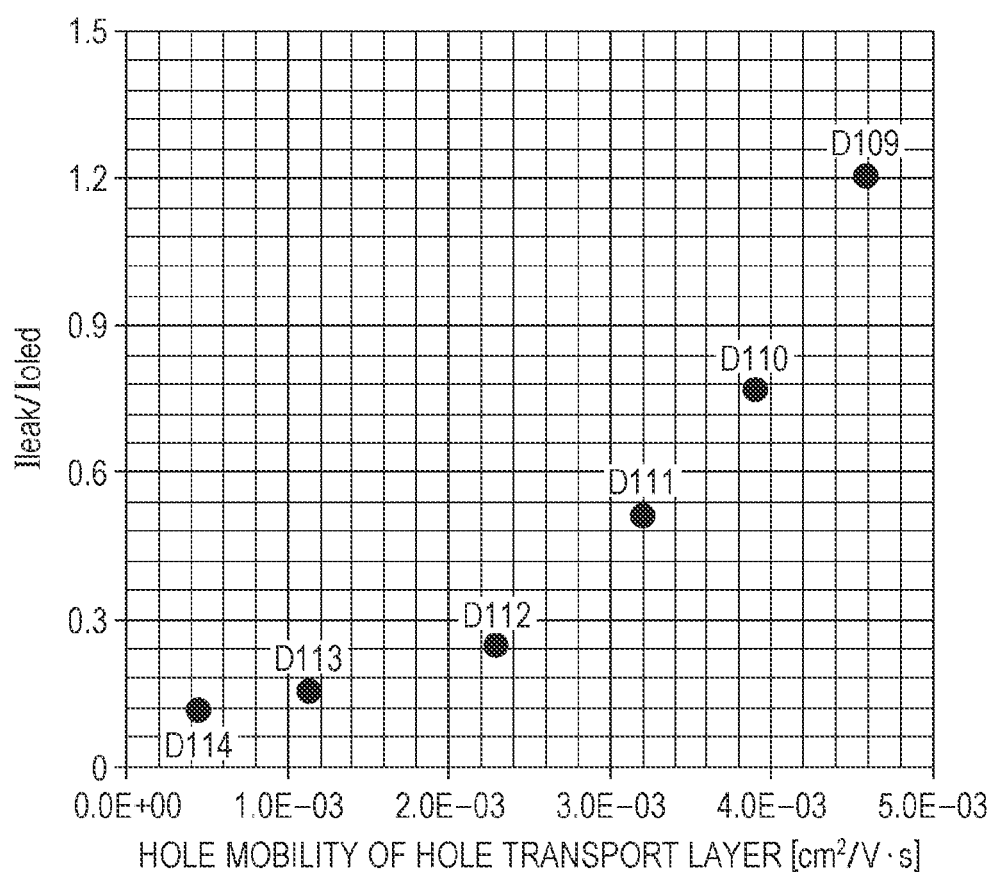
FIG. 4 is a plot showing the relationship between the hole mobility of the hole transport layer and the $I_{leak}/I_{oled}$ ratio of the leakage current $I_{leak}$ flowing from a target organic EL element to an adjacent organic EL element to the current $I_{oled}$ flowing into the target organic EL element.

FIG. 4 is a plot showing the relationship between the hole mobility of the hole transport layer and the $I_{leak}/I_{oled}$ ratio of the leakage current $I_{leak}$ flowing from a target organic EL element to an adjacent organic EL element to the current $I_{oled}$ flowing into the target organic EL element.

In an embodiment in which the hole transport region further includes an electron blocking layer, it is beneficial that the differences in ionization potential at the interface between the hole transport layer and the electron blocking layer and at the interface between the electron blocking layer and the first luminescent layer are each small from the viewpoint of reducing hole accumulation at the interfaces.

It is also beneficial that the layers from the reflection electrode to the first luminescent layer have a stepwise energy structure in which the ionization potential increases step by step from the reflection electrode to the first luminescent layer. More specifically, it is beneficial that the ionization potential of the hole transport layer lie between the work function of the reflection electrode and the ionization potential of the first luminescent layer. It is also beneficial that the ionization potential of the electron blocking layer lie between the ionization potential of the hole transport layer and the ionization potential of the first luminescent layer.

The ionization potentials of an organic compound layer containing a plurality of compounds can be estimated by photoelectron yield spectroscopy, photoelectron spectroscopy, or the like.

The properties such as hole mobility and ionization potential of the hole transport layer may be controlled by forming the hole transport layer of a mixture containing two or more hole transporting materials. Thus, the effective distance of the hopping site is increased and, consequently, the resistance at the side wall of the insulating layer is further increased. By adding a compound of the electron blocking layer into the hole transport layer, the ionization potential of the hole transport layer approaches the ionization potential of the electron blocking layer and, thus, hole accumulation at the interface between the hole transport layer and the electron blocking layer is reduced. If the compound used in the electron blocking layer has a high resistivity, the resistivity of the hole transport layer increases, and this is beneficial.

For example, the hole transport layer may contain a first compound and a second compound. In this instance, the hole mobility of the first compound may be $1.0 \times 10^{-3}$ cm$^2$/(V·s) or less, and, in some embodiments, it may be $5.0 \times 10^{-4}$ cm$^2$/(V·s) or less.

The highest occupied molecular orbital (HOMO) of the first compound may be lower than the HOMO of the second compound. The HOMO of the first compound may be 0.1 eV or more lower than the HOMO of the second compound.

The percentage of the weight of the first compound with respect to the total weight of the first compound and the second compound may be in the range of 50% to 95%, for example, 75% to 95%.

In an embodiment in which the hole transport region includes a hole injection layer, the hole injection layer is an organic compound layer disposed between the reflection electrode and the hole transport layer. The hole injection layer may contain a compound having an electron affinity of 5.0 eV or more. The thickness of the hole injection layer may be 10 nm or less from the viewpoint of reducing leakage current between the neighboring organic EL elements. The organic compound used in the hole injection layer may have a lowest unoccupied molecular orbital (LUMO) of −5.0 eV or less.

Examples of the compound having an electron affinity of 5.0 eV or more include hexaazatriphenylene derivatives and tetracyanoquinodimethane derivatives. In some embodiments, a hexacyano hexaazatriphenylene compound may be used.

The organic EL element includes at least one luminescent layer. If two or more luminescent layers are included, the two layers (a first and a second luminescent layer) may be separated by a further organic compound layer.

The first and the second luminescent layer may each emit light having any wavelength. For example, the first luminescent layer may emit blue light, and the second luminescent layer may emit green light and red light. Thus, the organic EL element may emit white light. Alternatively, the first luminescent layer may emit green light and red light for an organic EL element operable to emit white light. The emission color of the first luminescent layer and the emission color of the second luminescent layer may be complementary to each other for emitting white light. In some embodiments, the first luminescent layer does not emit blue light: hence, the first luminescent layer emits light other than blue light. If a luminescent layer operable to emit blue light is close to a metal electrode, surface plasmon loss increases, and the power consumption of the device increases accordingly. A luminescent layer operable to emit blue light implies that the luminescent layer contains a luminescent material capable of emitting blue light.

From the viewpoint of reducing the power consumption of the light-emitting device, the luminous efficiency of the light-emitting device may be increased by optical interference.

In the present disclosure, the luminescent layer is of an electron trapping type so as to maintain the optical path length enabling the emission from the luminescent layer to be enhanced even though the thickness of the hole transport region is reduced. Since the electrode-trapping luminescent layer emits light mainly on the side toward the negative electrode, the distance from the emission point to the reflection electrode is the sum of the thickness of the hole transport region and the thickness of the luminescent layer. Therefore, even if the thickness of the hole transport region is reduced, the thickness of the luminescent layer compensates for the reduction, thus maintaining the distance for optical interference.

Thus, the first luminescent layer is an electron-trapping luminescent layer. The electron-trapping luminescent layer mentioned herein contains a first compound and a second compound, and the compound having a higher weight has a lower electron affinity than the other. The electron affinity of a compound may be estimated by the lowest unoccupied molecular orbital (LUMO) level of the molecule of the compound. When the electron affinities are estimated by LUMO, one of the compounds having a higher weight than the other in the electron-trapping luminescent layer has a higher LUMO level than the other. A higher LUMO level is closer to the vacuum level, and a high LUMO level may be referred to as a shallow LUMO level or a small absolute value of LUMO level. In general, electron affinity is represented by an absolute value, and LUMO level is represented by a real number. More specifically, electron affinity is represented by a positive number, and LUMO level is represented by a negative number.

For the electron-trapping luminescent layer, the first compound may be selected from among pyrene derivatives, anthracene derivatives, fluorene derivatives, and naphthalene derivatives. If the first compound accounts for the largest part of the weight of the luminescent layer, the first compound is referred to as the host material or the host.

The second compound may be selected from among pyrene derivatives, fluoranthene derivatives, fluorene derivatives, and chrysene derivatives. A derivative of the first compound or the second compound refers to a form whose base skeleton has a substituent or a condensed ring. For example, fluoranthene derivatives include benzofluoranthene, dibenzofluoranthene, and indenobenzo[k]fluoranthene. If the first compound is the host, the second compound is referred to as a dopant or a guest.

The substituents of derivatives may include alkyl groups, aryl groups having a carbon number of 6 to 60, and heteroaryl groups having a carbon number of 6 to 60.

The distance between the first luminescent layer and the reflection electrode may satisfy the following relationship (2) from the viewpoint of enhancing the emission from the first luminescent layer. The smaller the thickness of the first luminescent layer, the better. However, even if the thickness of the first luminescent layer is large, leakage current in the light-emitting device can be reduced because the influence of the luminescent layer on leakage current is small.

$$(0.12-(\varphi_r/4\pi))<L/\lambda_1<(0.18-((\varphi_r/4\pi)) \quad (2)$$

Here $\lambda_1$ represents the shortest of the wavelengths at which an emission spectrum of the first luminescent layer has peaks, and $\varphi_r$ represents the phase shift at the reflection electrode.

When relationship (2) holds true, surface plasmon loss is reduced to reduce the power consumption of the light-emitting device.

In the embodiment in which the hole transport region includes a hole transport layer and an electron blocking layer, the first luminescent layer may satisfy the following relationship (3):

$$d_{(1st\text{-}EML)} > d_{(HTL)} + d_{(EBL)} \quad (3),$$

wherein $d_{(1st\text{-}EML)}$ represents the thickness of the first luminescent layer, and $d_{(HTL)}$ and $d_{(EBL)}$ represent the thickness of the hole transport layer and the thickness of the electron blocking layer, respectively.

The thickness of the first luminescent layer may be 35 nm or less. When the thickness of the first luminescent layer is 35 nm or less, leakage current between neighboring organic EL elements is further reduced. This will be verified herein later.

In an embodiment, the organic EL element may further include an electron transport layer between the luminescent layer and the light extraction electrode. The material of the electron transport layer is selected in view of the balance with the hole mobility of the hole transport layer. The material of the electron transport layer may be selected from a group including aromatic hydrocarbons such as chrysene derivatives, fluoranthene derivatives, and anthracene derivatives; heterocyclic compounds such as phenanthroline derivatives, diazafluoranthene derivatives, and azaanthracene derivatives; and organic metal complexes such as tris(8-hydroxyquinolinato)aluminum (Alq3), beryllium complexes, and magnesium complexes.

The R, G, and B sub pixels are arranged in a stripe array, a square array, a delta array, or a Bayer array.

In some embodiments, the reflection electrode of the organic EL element may be made of a metal material having a reflectance of 80% or more. More specifically, the material of the reflection electrode may be a metal, such as Al or Ag, or an alloy thereof with Si, Cu, Ni, Nd, Ti, or the like. The term reflectance mentioned here refers to the reflectance at the emission wavelength of the luminescent layer. The reflection electrode may include a barrier layer on the side toward the light extraction electrode. The barrier layer may be made of a metal, such as Ti, W, Mo, or Au, or an alloy thereof.

The insulating layer of the organic EL element of the present disclosure may be formed of silicon nitride (SiN), silicon nitroxide (SiON), or silicon oxide (SiO) by chemical vapor deposition (CVD).

From the viewpoint of increasing the resistance of the organic compound layer in the region between organic EL elements, the thickness of the organic compound layer at the side wall of the insulating layer may be smaller than that in the aperture region. There are emission points of the organic EL element in the aperture region. More specifically, the thickness of the organic compound layer at the side wall may be reduced by increasing the angle between the substrate and the side wall of the insulating layer or increasing the thickness of the insulating layer. The angle between the substrate and the side wall of the insulating layer may be referred to as taper angle of the insulating layer.

The angle between the substrate and the side wall of the insulating layer may be in the range of 60 degrees to 90 degrees. Also, the thickness of the insulating layer may be in the range of 40 nm to 150 nm.

The insulating layer may have a groove between the reflection electrode and the adjacent reflection electrode. The presence of the groove helps reduce the thickness of the organic compound layer and increase the resistance.

In an embodiment, the light extraction electrode of the organic EL element may be a semi-transmissive reflection layer that transmits a portion of the light incident on the surface thereof and reflects the other portion (that is, has transmission and reflection characteristics). The light extraction electrode is made of, for example, an elemental metal, such as magnesium or silver, or an alloy containing mainly magnesium or silver or containing an alkali metal or an alkaline-earth metal. The light extraction electrode may have a multilayer structure provided that it has a favorable transmittance.

The sealing layer of the organic EL element may be formed by chemical vapor deposition (CVD) or atomic layer deposition (ALD). The sealing layer may be made of a material having a very low permeability to external oxygen and moisture, such as silicon nitride (SiN), silicon nitroxide (SiON), aluminum oxide, silicon oxide, or titanium oxide. The sealing layer may be a single-layer or a multilayer structure provided that it can sufficiently block moisture. If the sealing layer has a multilayer structure, it may be defined by a combination of a SiN layer and an aluminum oxide layer. The multilayer structure may include three or more layers.

In an embodiment, the hole transport region of the organic EL element may contain any of the following compounds HT1 to HT38:

HT-1
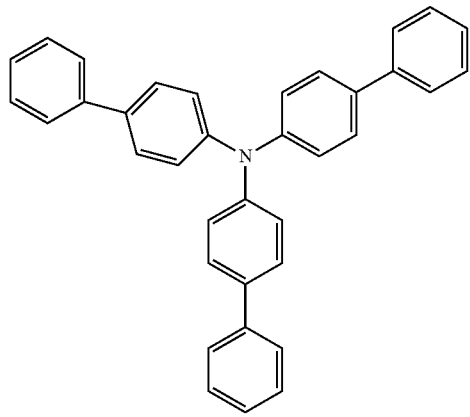
HT-1
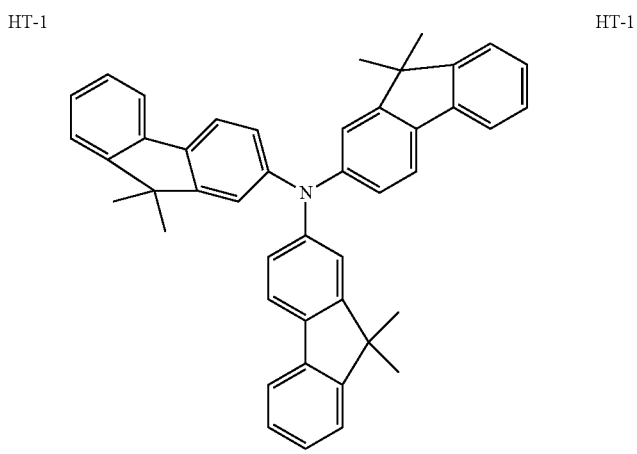
HT-3
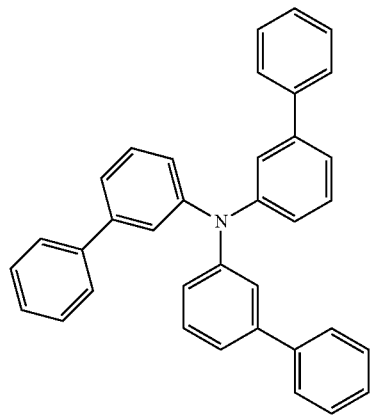
HT-4
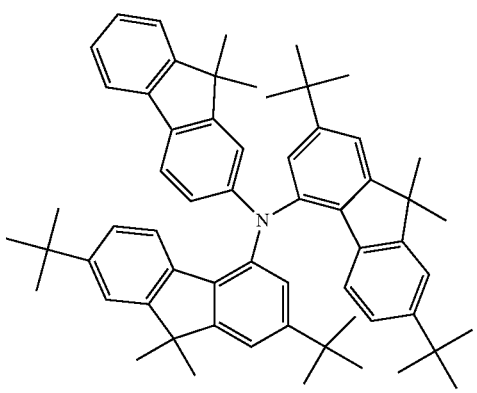
HT-5
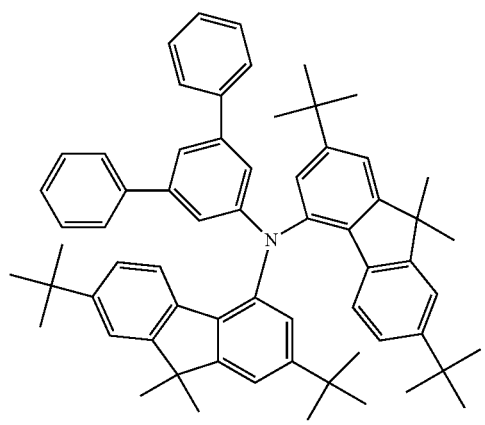
HT-6
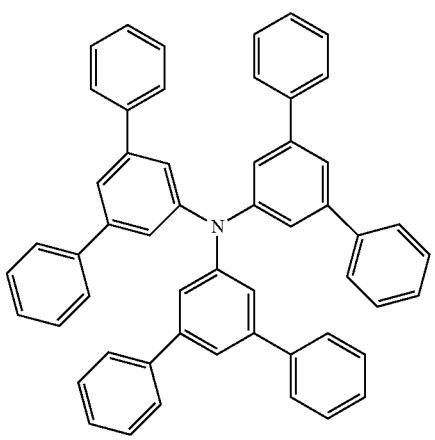

-continued
HT-7
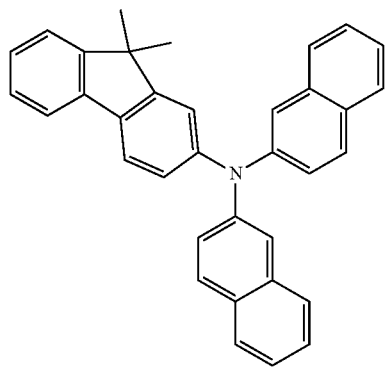
HT-8
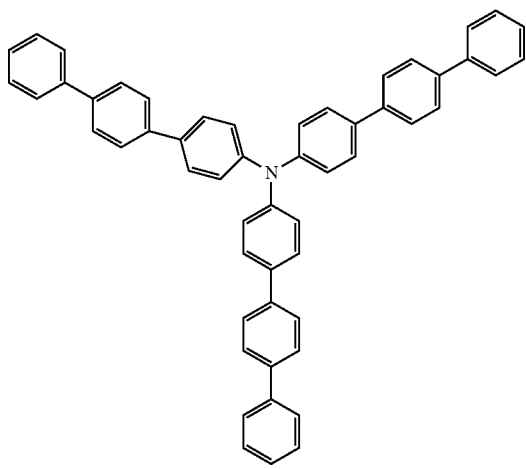
HT-9
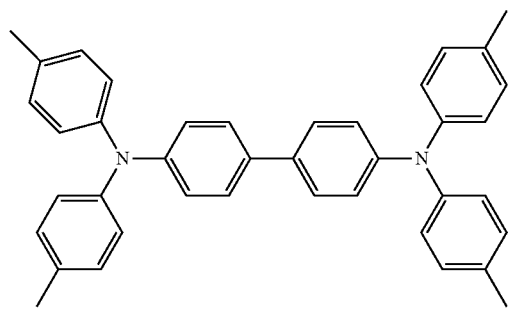
HT-10
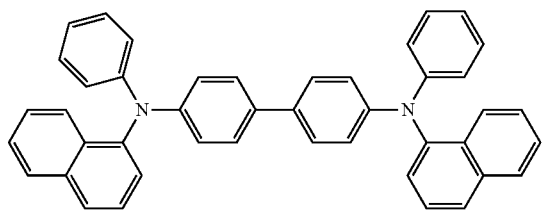
HT-11
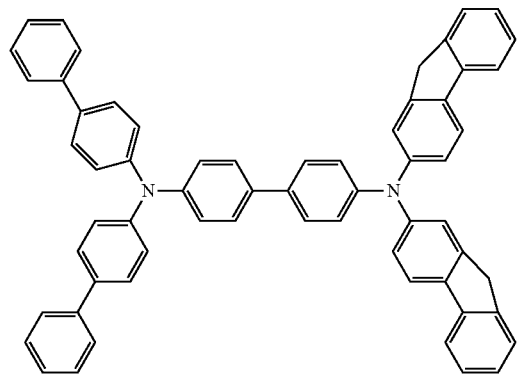
HT-12
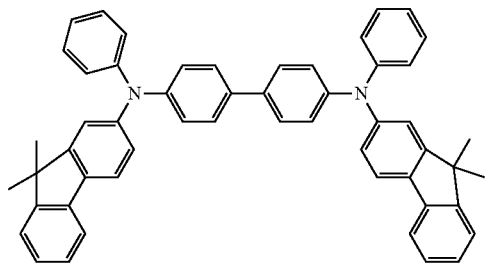
HT-13
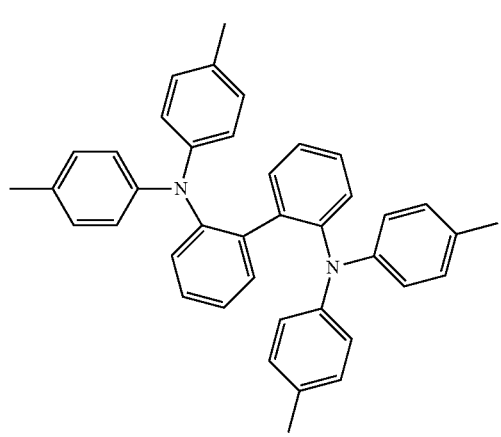

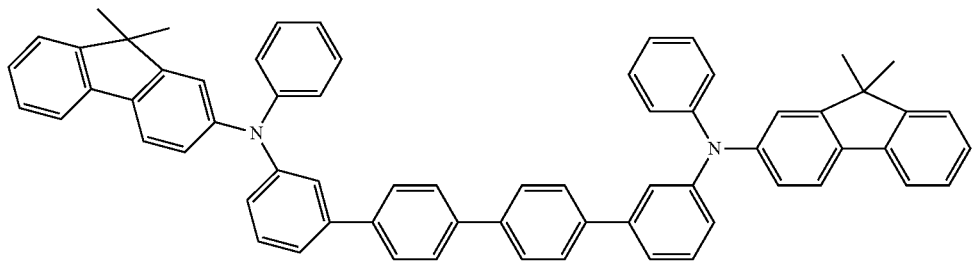
HT-14
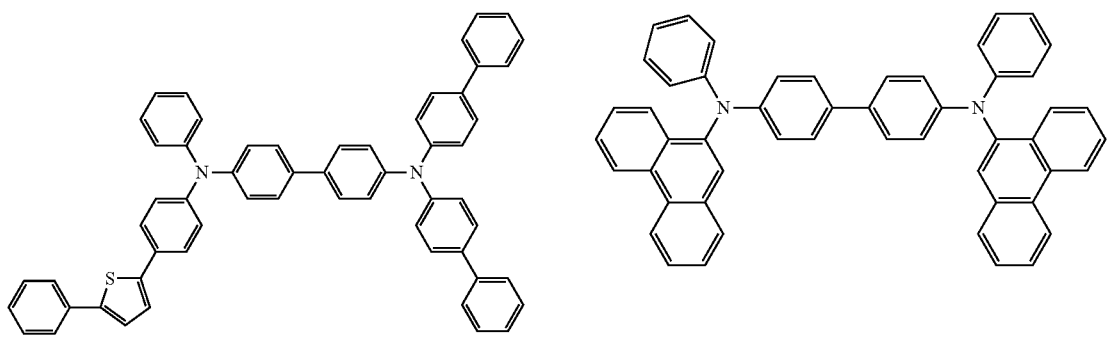
HT-15
HT-16
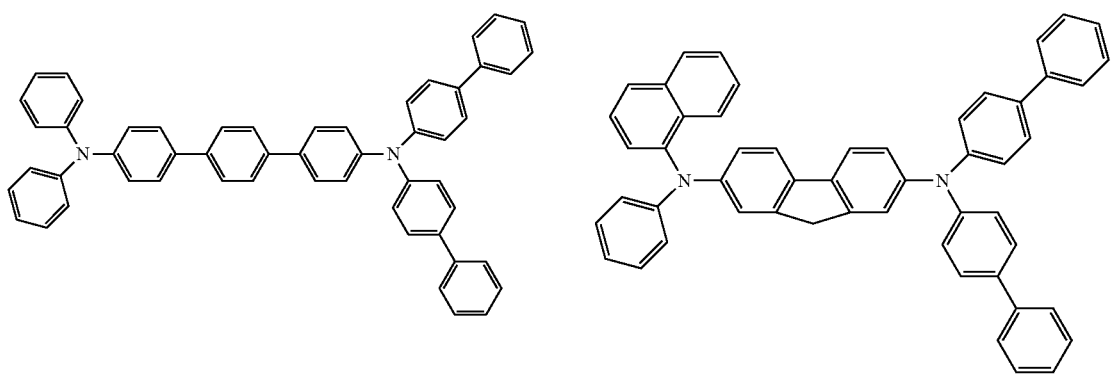
HT-17
HT-18
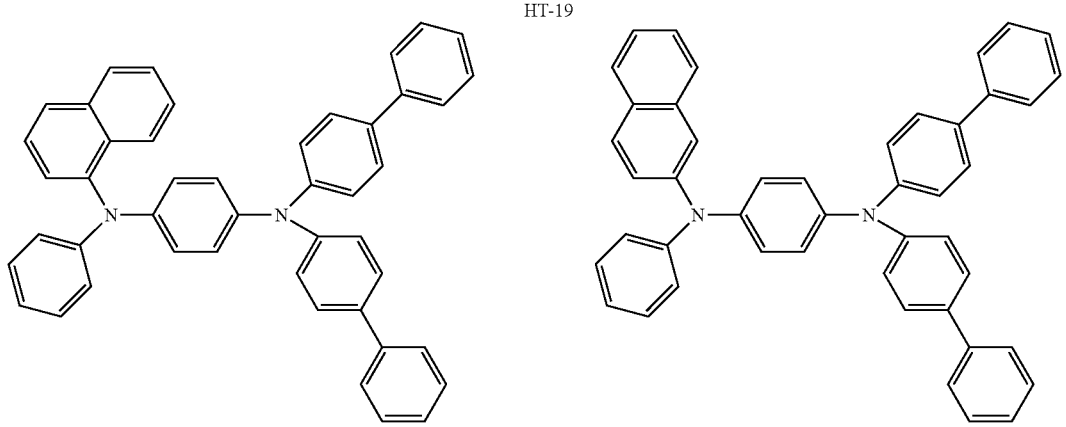
HT-19
HT-20

-continued
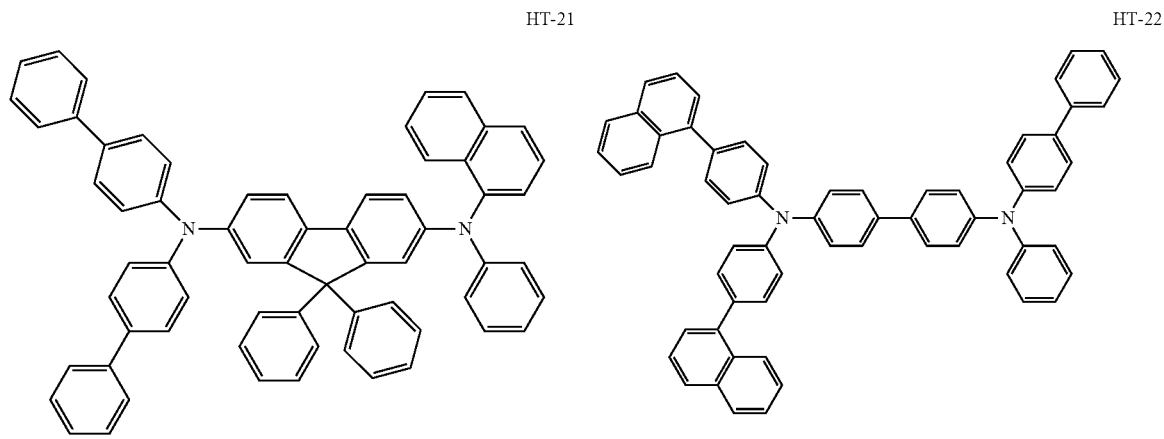
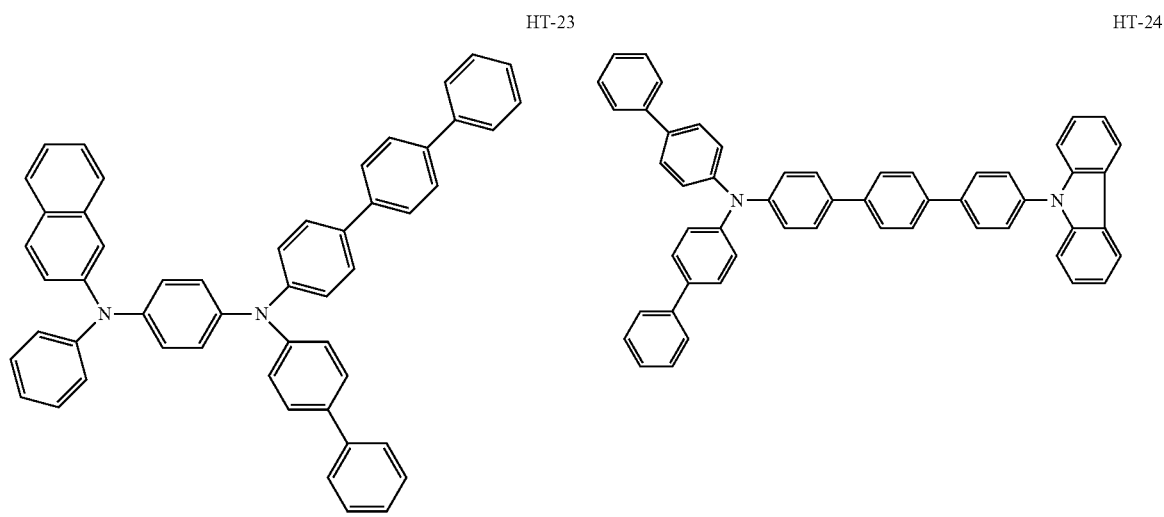
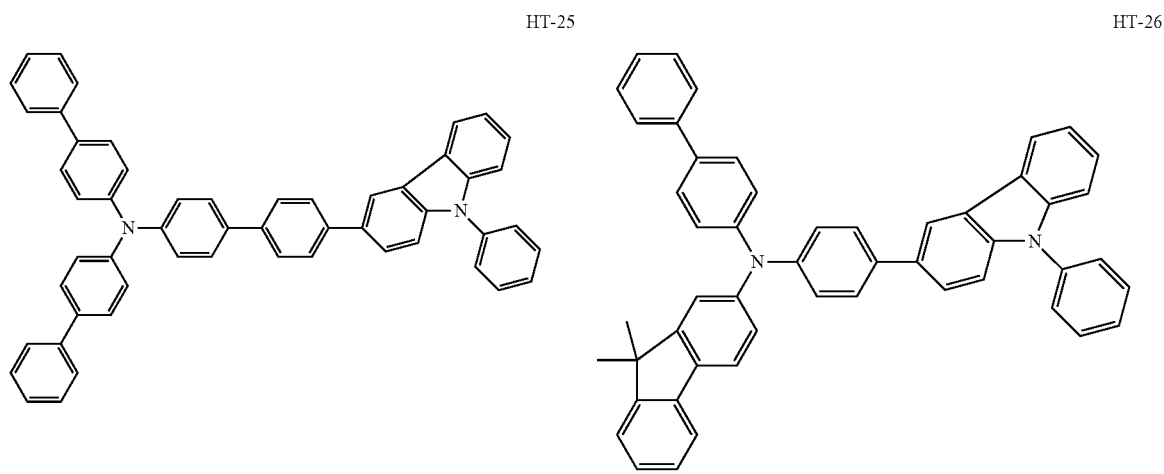

HT-27
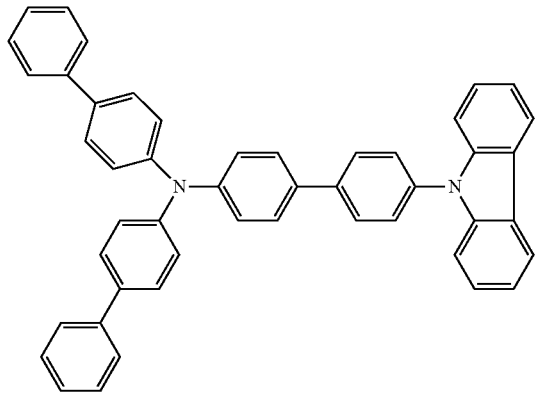
HT-28
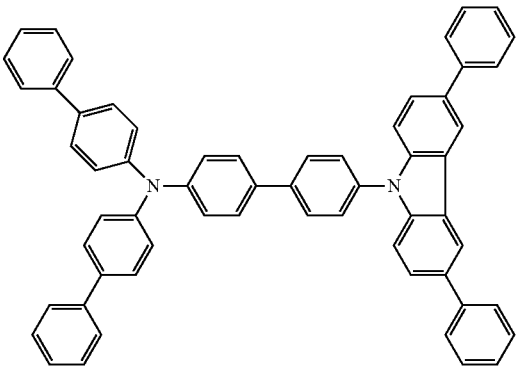
HT-29
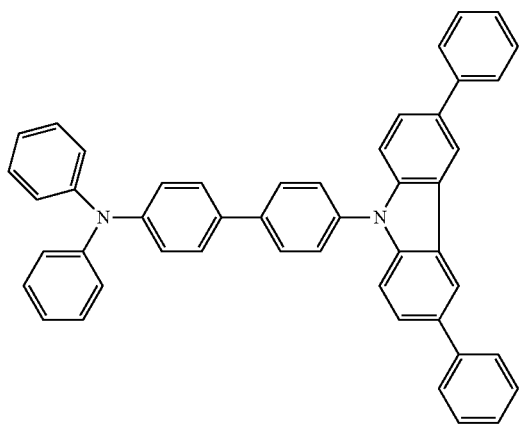
HT-30
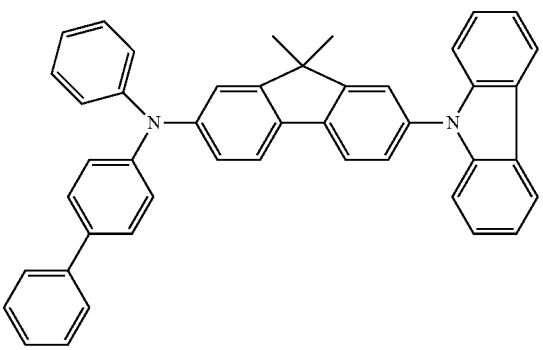
HT-31
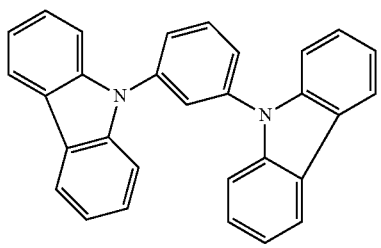
HT-32
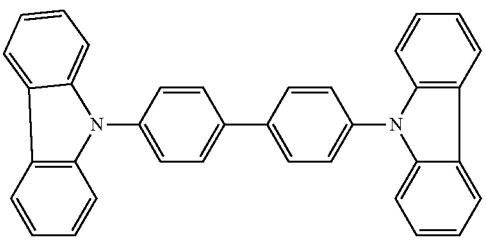
HT-33
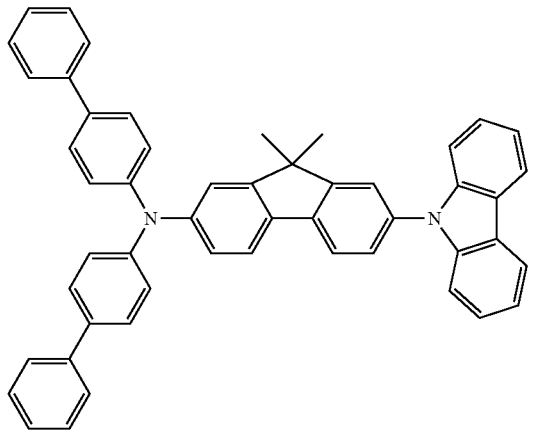
HT-34
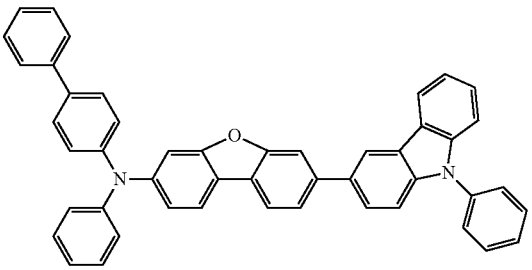

HT-35
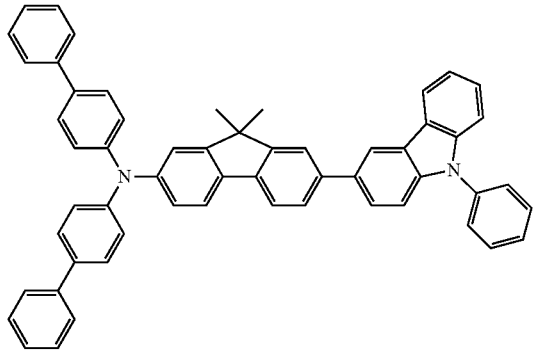

HT-36
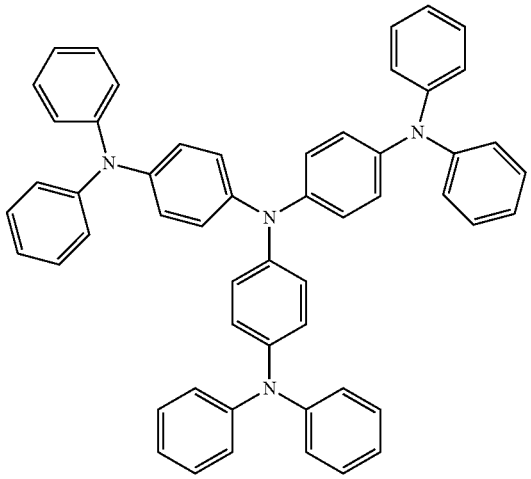

HT-37
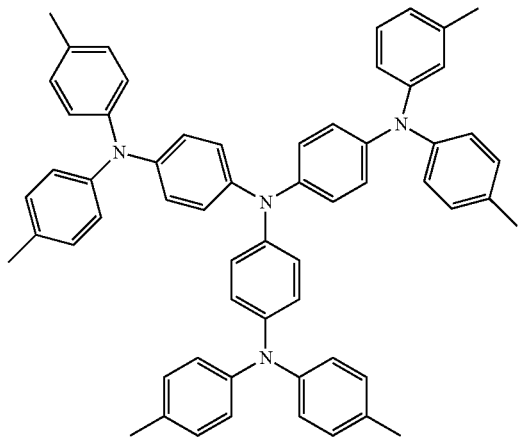

HT-38
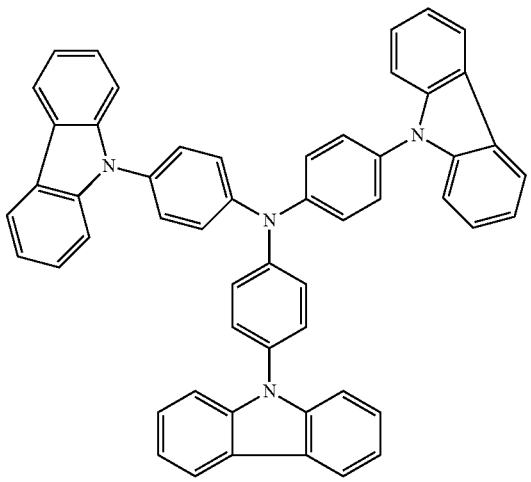

The compound used in the hole transport region may be represented by one of the following general formulas [1] and [2]:

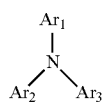
[1]

wherein $Ar_1$ to $Ar_3$ each represent one independently selected from the group consisting of substituted or unsubstituted aryl groups including phenyl, bisphenyl, terphenyl, fluorenyl, naphthyl, and spirofluorenyl and substituted or unsubstituted heterocyclic groups including dibenzofuranyl, dibenzothiophenyl, thiophenyl, furanyl, and carbazolyl; and

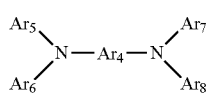
[2]

wherein $Ar_4$ represents a substituted or unsubstituted aryl group selected from the group consisting of phenyl, biphenyl, terphenyl, fluorenyl, dibenzofuranyl, dibenzothiophenyl, and naphthyl, and $Ar_5$ to $Ar_8$ each represent one independently selected from the group consisting of substituted or unsubstituted aryl groups including phenyl, biphenyl, terphenyl, fluorenyl, phenanthrenyl, and pyrenyl and substituted or unsubstituted heterocyclic groups including dibenzofuranyl, dibenzothiophenyl, thiophenyl, furanyl, and carbazolyl.

The light-emitting device may be used in a display device including an active element, such as a transistor. The display device includes a lateral driving circuit, a vertical driving circuit, and a display section, and the display section includes the light-emitting device according to an embodiment of the present disclosure.

Figure 3:
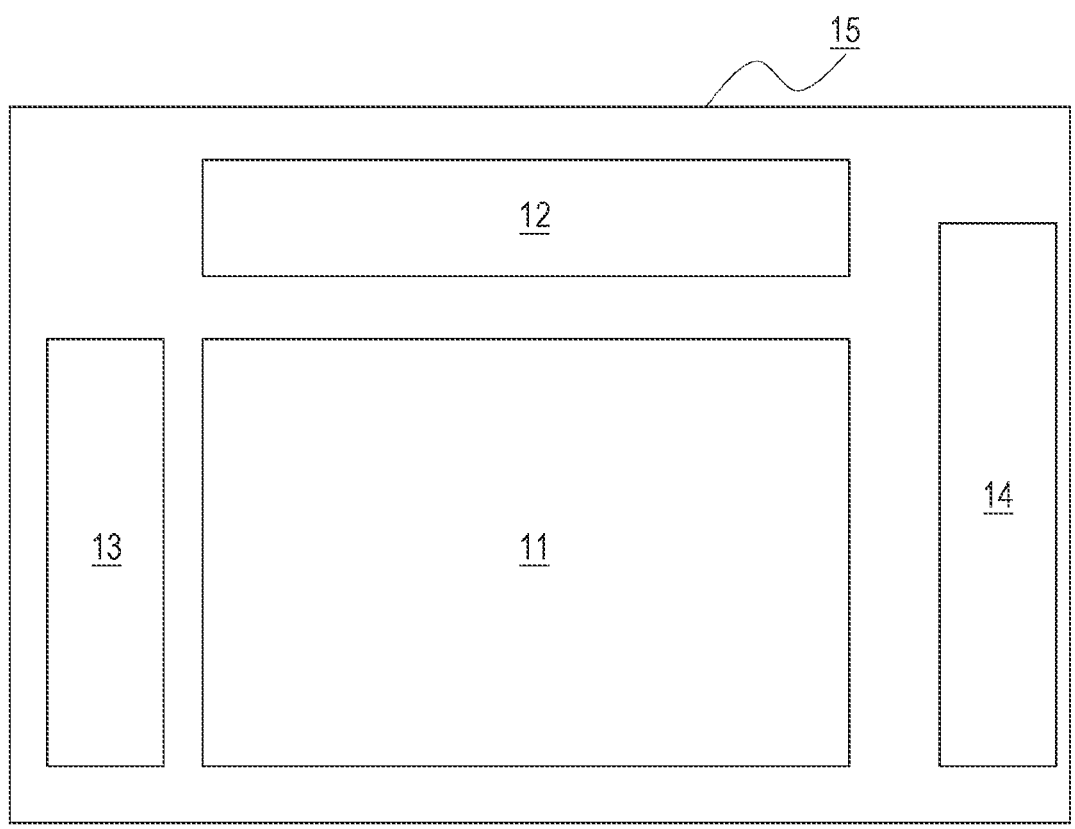
FIG. 3 is a schematic diagram of a display device according to an embodiment of the present disclosure.

FIG. 3 is a schematic diagram of a display device according to an embodiment of the present disclosure. The display device 15 includes a display region 11, a lateral driving circuit 12, a vertical driving circuit 13, and a connecting section 14. The display region 11 may have the light-emitting device according to an embodiment of the present discloser.

In an embodiment, the display device may be used as a display section of an image forming apparatus, such as a multifunctional printer or an ink jet printer. In this instance, the display section may have both a displaying function and an operational function.

In an embodiment, the display device may be used as a display section of an imaging apparatus, such as a camera, including an optical system having a plurality of lenses and an imaging element capable of receiving light that has passed through the optical system. The display section of the imaging apparatus may be used to display information obtained by the imaging element. The display section may be exposed to the outside of the imaging apparatus or may be disposed within a viewfinder.

In an embodiment, the display device may include a red, a green, and a blue color filter. The red, green, and blue color filters may be arranged in a delta array.

In an embodiment, the display device of the present disclosure may be used in the display section of a mobile terminal. In this instance, the display section may have both a displaying function and an operational function.

An organic EL element according to an embodiment will now be described.

The organic EL element includes a pair of electrodes (anode and cathode) and an organic compound layer between the electrodes. The organic compound layer may be composed of a single layer or have a multilayer structure including a plurality of layers, provided that the organic compound layer includes a luminescent layer.

The luminescent layer may contain a host and a guest. The luminescent layer may also contain an assist. The host mentioned here refers to a compound accounting for the highest percentage of the total weight of the compounds in the luminescent layer. The guest mentioned here refers to a compound in the luminescent layer having a lower weight than the host and is responsible for main emission. The assist material mentioned here refers to a compound in the luminescent layer having a lower weight than the host and helps the guest emit light. The assist material may be referred to as a second host. If the luminescent layer of the organic luminescent element has a uniform composition throughout the layer, the composition of the entire luminescent layer can be determined by analyzing a portion of the luminescent layer.

When the organic compound disclosed herein is used as the guest of the luminescent layer, the guest content may be in the range of 0.01% by weight to 20% by weight, for example, 0.1% by weight to 5% by weight, relative to the total weight of the luminescent layer.

Also, when the luminescent layer contains a host and a guest, the host may be a compound having a higher LUMO level than the guest. This is because the electron trap type guest has a low LUMO, and by using a compound having a higher LUMO than the organic compound of the present disclosure as the host, the organic compound of the present disclosure can receive a larger part of the electrons applied to the host.

The luminescent layer may be composed of a single layer or may have a multilayer structure. Also, the luminescent layer may contain another luminescent material having another emission color to emit a color light mixed with red that is the emission color of the present disclosure. The multilayer structure refers to a state where different luminescent layers are formed one on top of another. In this instance, the emission color of the organic luminescent element is not limited to red. For example, the emission color may be white or intermediate color. If the emission color is white, the additional luminescent layer emits a color light other than red light, such as blue or green. The luminescent layer may be formed by vapor deposition or coating. The organic compound of the present disclosure may be used in other organic compound layers of the organic luminescent element as well as in the luminescent layer. For example, the electron transport layer, the electron injection layer, the hole transport layer, the hole injection layer, the hole blocking layer, or any other layer may contain the organic compound of the present disclosure. In this instance, the emission color of the organic luminescent element is not limited to red. For example, the emission color may be white or intermediate color.

The organic compound may be used in combination with one or more known low-molecular-weight or polymeric compounds used as a hole injecting or a hole transporting material, a host, a luminescent material, an electron injecting or an electron transporting material, and the like, if necessary.

These compounds are as follows. The hole injecting or transporting material may have so high a hole mobility as facilitates hole injection from the anode and as enables the injected holes to be transported to the luminescent layer. Also, from the viewpoint of reducing the crystallization or any other deterioration of the material in the organic luminescent element, the hole injecting or transporting material may have a high glass transition temperature. Low-molecular-weight or polymeric hole injecting or transporting materials include triarylamine derivatives, arylcarbazole derivatives, phenylenediamine derivatives, stilbene derivatives, phthalocyanine derivatives, porphyrin derivatives, poly(vinyl carbazole), polythiophene, and other electrically conductive polymers. The hole injecting or transporting material may also be used in the electron blocking layer.

The electron transporting material may be a compound capable of transporting electrons injected from the cathode to the luminescent layer and may be selected in view of the balance with the hole mobility of the hole transporting material. Electron transporting materials include oxadiazole derivatives, oxazole derivatives, pyrazine derivatives, triazole derivatives, triazine derivatives, quinoline derivatives, quinoxaline derivatives, phenanthroline derivatives, organic aluminum complexes, and condensed ring compounds (such as fluorene derivatives, naphthalene derivatives, chrysene derivatives, and anthracene derivatives). The electron transporting material may also be used in the hole blocking layer.

Figure 6:
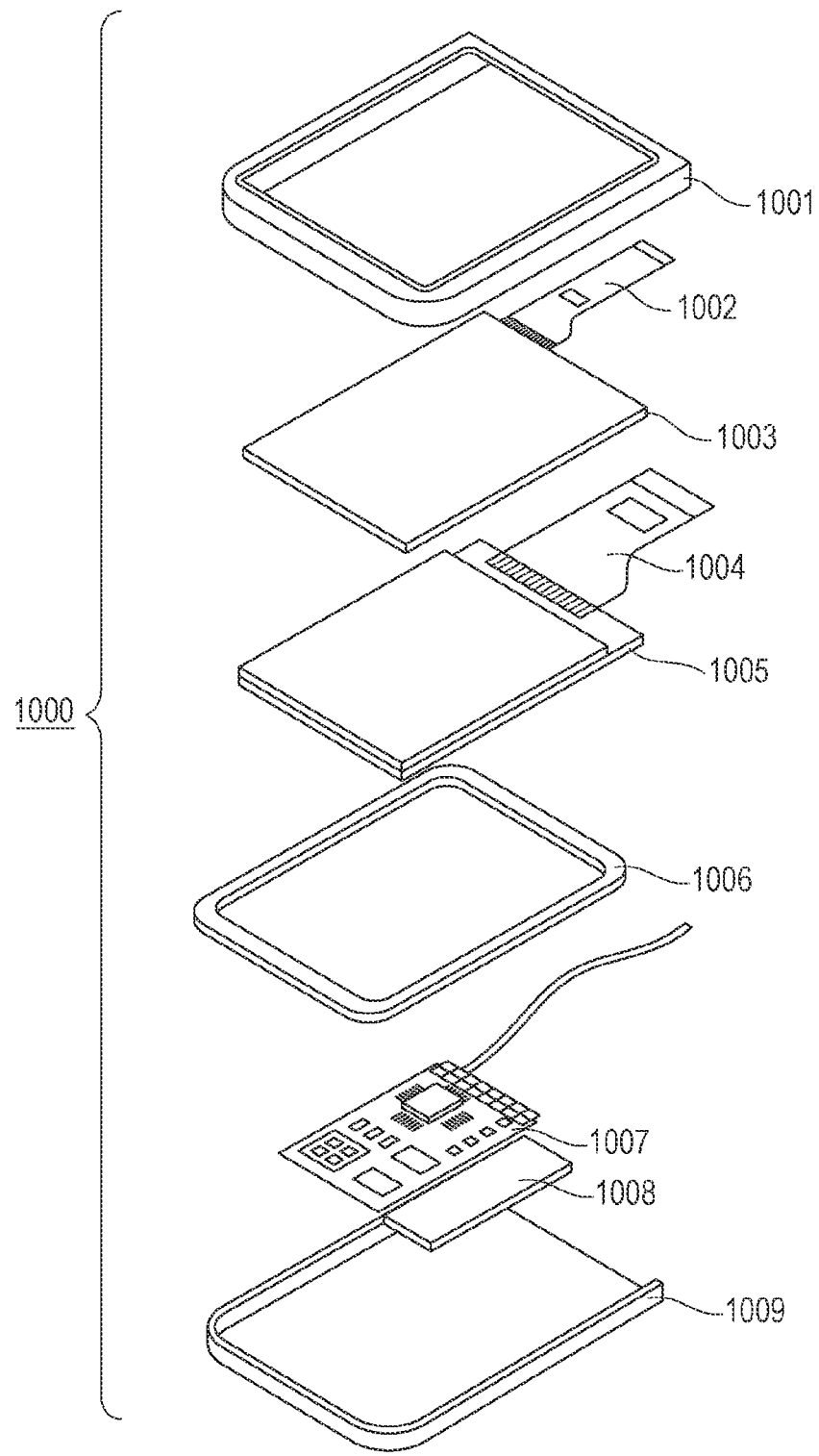
FIG. 6 is a schematic illustrative representation of a display device according to an embodiment of the present disclosure.

FIG. 6 is a schematic illustrative representation of a display device according to an embodiment of the present disclosure. The display device 1000 may include a touch panel 1003, a display panel 1005, a frame 1006, a circuit board 1007, and a battery 1008 between an upper cover 1001 and a lower cover 1009. The touch panel 1003 and the display panel 1005 are connected to a flexible printed circuits (FPCs) 1002 and 1004, respectively. Transistors are printed on the circuit board 1007. The battery 1008 is not necessarily provided unless the display device is for mobile use, and the position of the battery is not limited to the position shown in the figure even for mobile use.

In an embodiment, the display device of the present disclosure may be used as a display section of an imaging apparatus including an optical system having a plurality of lenses and an imaging element capable of receiving light that has passed through the optical system. The display section of the imaging apparatus may be used to display information obtained by the imaging element. The display section may be exposed to the outside of the imaging apparatus or may be disposed within a viewfinder. The imaging apparatus may be a digital camera or a digital video camera.

Figure 7:
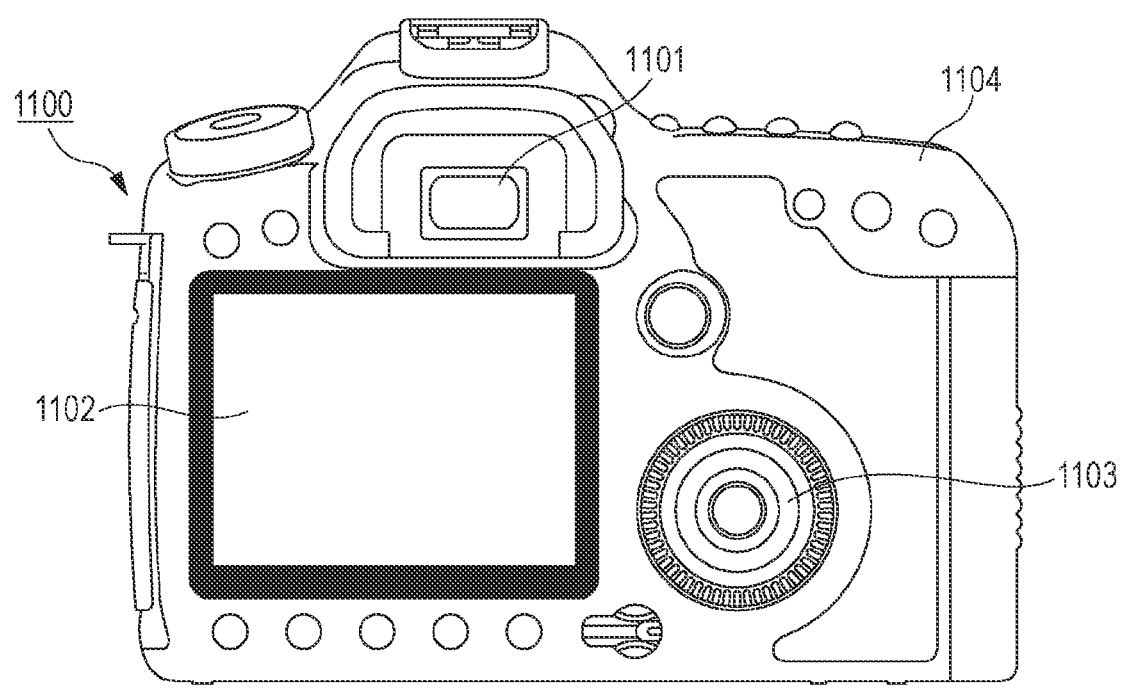
FIG. 7 is a schematic view of an imaging apparatus according to an embodiment of the present disclosure.

FIG. 7 is a schematic view of an imaging apparatus according to an embodiment of the present disclosure. The imaging apparatus 1100 may include a viewfinder 1101, a rear display 1102, an operational section 1103, and a housing 1104. The viewfinder 1101 may include the display device according to an embodiment of the present disclosure. In this instance, the display device may display not only taken images but also environmental information, imaging instructions, or the like. The environmental information may include, for example, the intensity and the direction of external light, the moving speed of a subject to be taken, and the possibility that the subject is hidden by an object.

Since the appropriate timing for taking an image is a very short period of time, it is desirable to display information as quickly as possible. Accordingly, the display device using organic EL elements according to an embodiment of the present disclosure is useful. This is because organic EL elements respond quickly. The display device using organic EL elements is more suitable than liquid crystal display devices for use in apparatuses required to display information quickly.

The imaging apparatus 1100 includes an optical system (not shown). The optical system includes a plurality of lenses and forms an image on the imaging element in the housing 1103. The focus can be adjusted by adjusting the relative positions of the plurality of lenses. This may be automatically performed.

In an embodiment, the display device may include a red, a green, and a blue color filter. The red, green, and blue color filters may be arranged in a delta array.

In an embodiment, the display device of the present disclosure may be used in the display section of a mobile terminal. In this instance, the display section may have both a displaying function and an operational function. The mobile terminal may be a cellular phone, such as a smartphone, a tablet PC, a head-mounted display, or the like.

Figure 8:
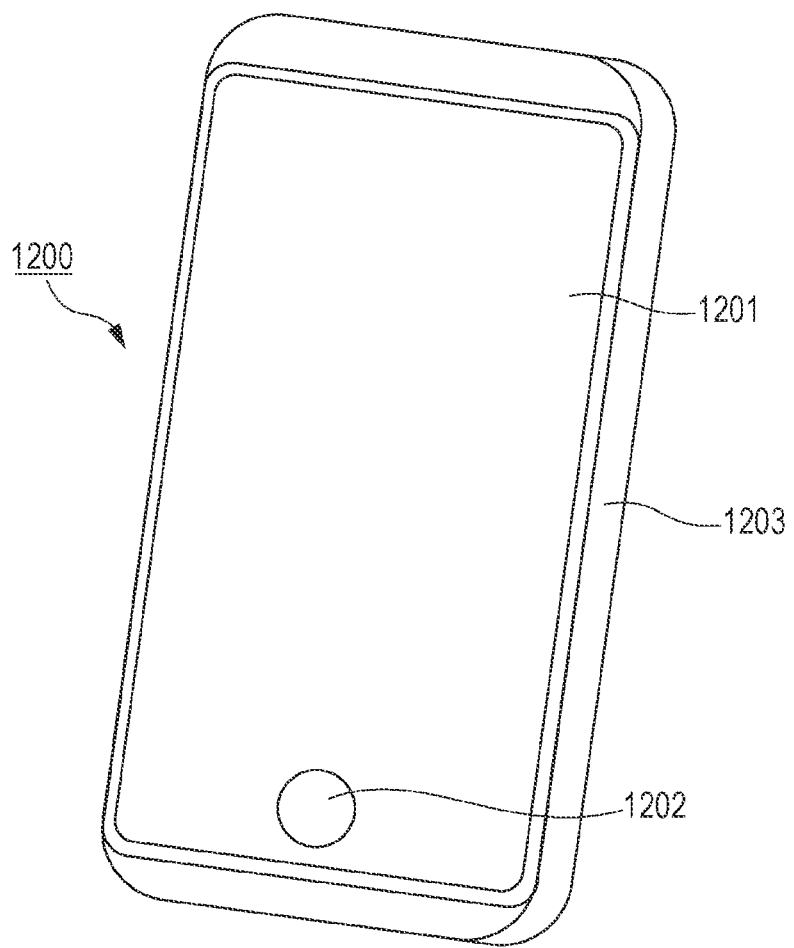
FIG. 8 is a schematic view of a mobile apparatus according to an embodiment of the present disclosure.

FIG. 8 is a schematic view of an electric apparatus according to an embodiment of the present disclosure. The mobile apparatus 1200 includes a display section 1201, an operational section 1202, and a housing 1203. The housing 1203 contains a circuit, a printed board having the circuit, a battery, and a communication section. The operational section 1202 may be a button or a touch panel responder. The operational section 1202 may have a biometrically authenticating function of recognizing the fingerprint and releasing the lock. The mobile apparatus including a communication section may be referred to as a communication apparatus.

Figure 9A:
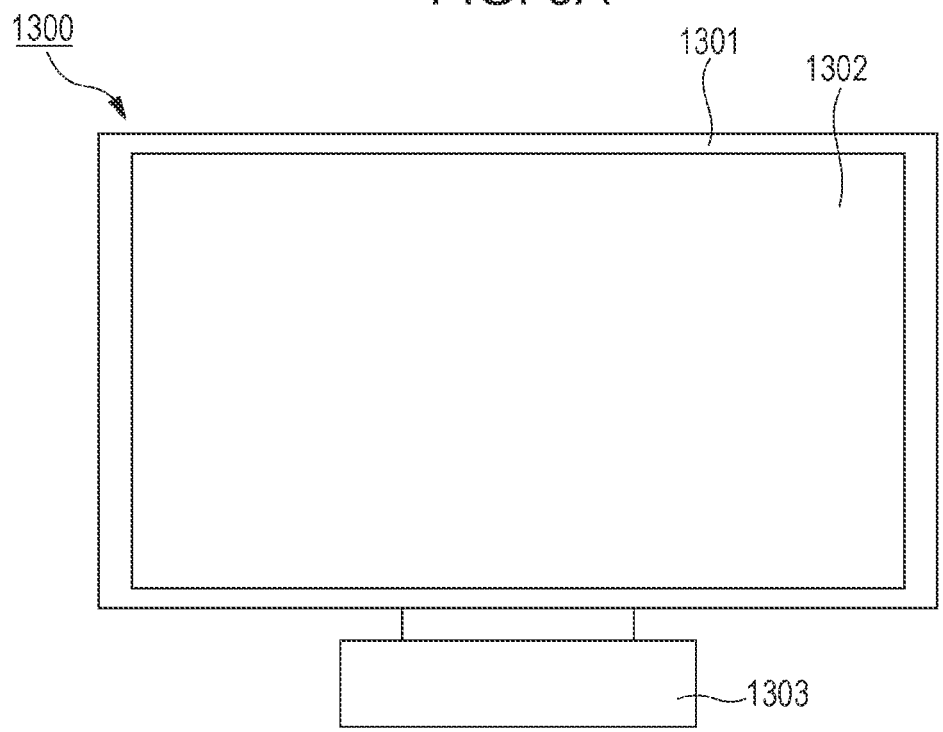
FIG. 9A is a schematic view of a display device according to an embodiment of the present disclosure.
Figure 9B:
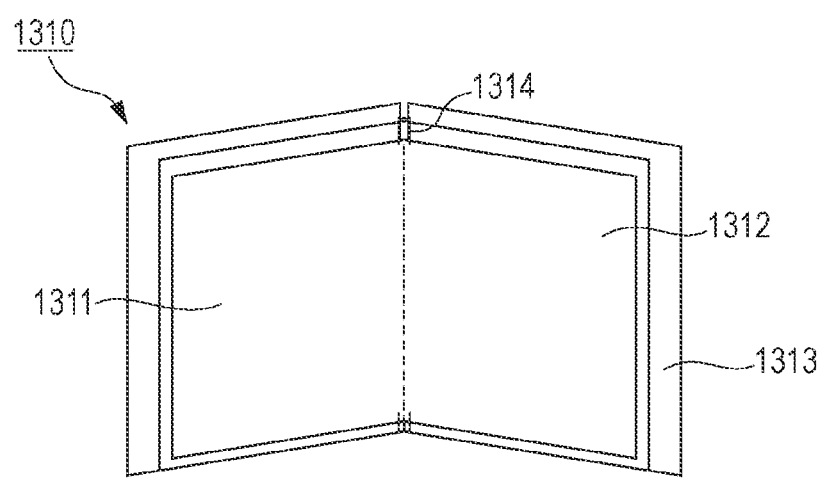
FIG. 9B is a schematic view of a foldable display device according to an embodiment of the present disclosure.

FIGS. 9A and 9B are schematic illustrative representations of display devices each according to an embodiment of the present disclosure. FIG. 9A shows a display device used as a TV monitor or a PC monitor. This display device 1300 includes a frame 1301 and a display section 1302. The display section 1302 may include the light-emitting device according to an embodiment of the present disclosure.

The display device also includes a base 1303 supporting the frame 1301 and the display section 1302. The base 1303 is not limited to the form shown in FIG. 9A. Alternatively, the lower side of the frame 1301 may serve as the base.

The frame 1301 and the display section 1302 may be curved. The radius of curvature thereof may be in the range of 5000 mm to 6000 mm.

FIG. 9B is a schematic illustrative representation of a display device according to another embodiment of the present disclosure. The display device 1310 shown in FIG. 9B is a foldable display device. The display device 1310 includes a first display section 1311, a second display section 1312, and a housing 1313 and has a folding line 1314. The first display section 1311 and the second display section 1312 each may include the light-emitting device according to an embodiment of the present disclosure. The first display section 1311 and the second display section 1312 may be continuous without being separated by a joint. The first display section 1311 and the second display section 1312 may be separated from each other along the folding line 1314. The first display section 1311 and the second display section 1312 may display different images from each other, or a single image may be displayed on a set of the first and second display sections.

Figure 10:
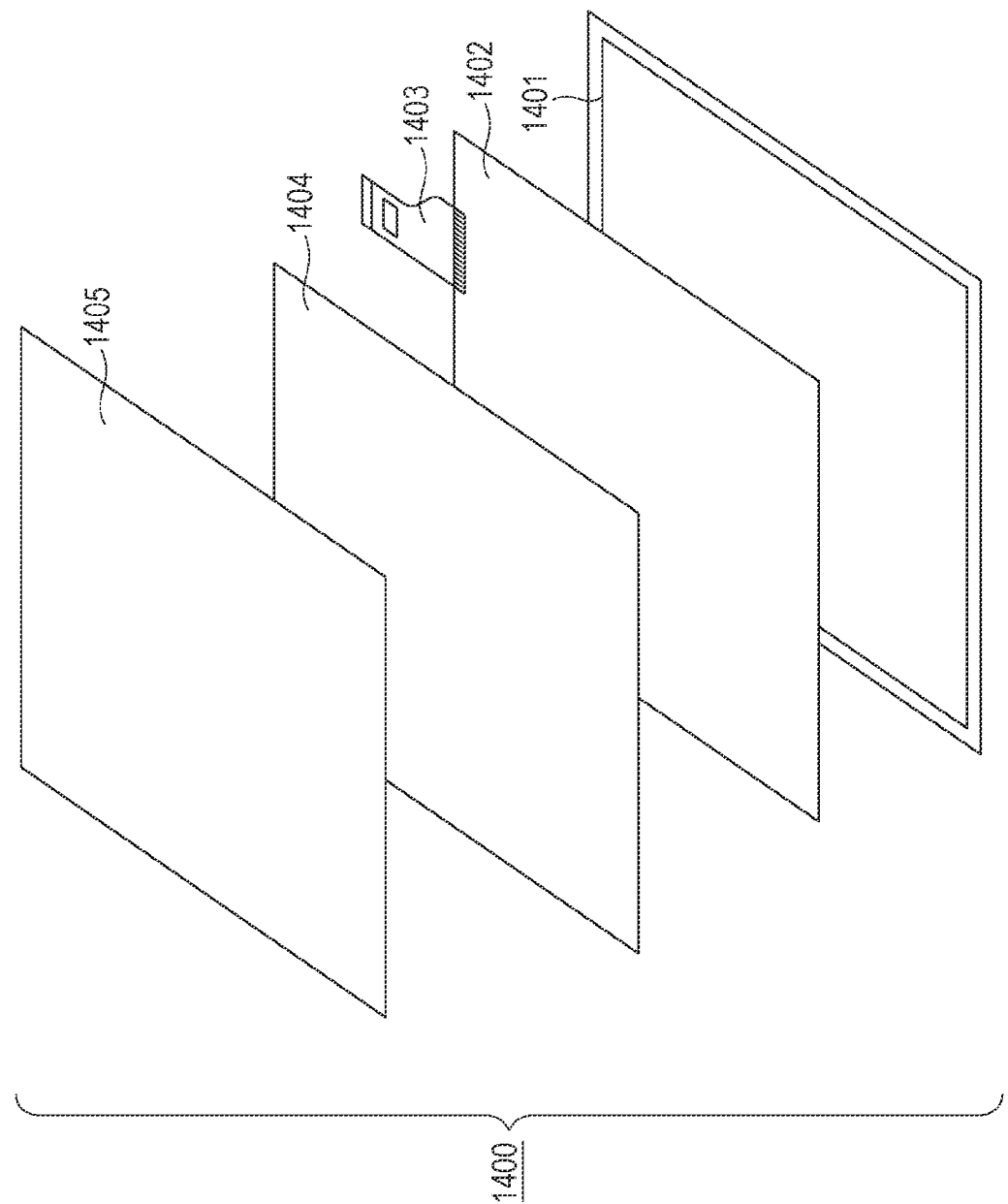
FIG. 10 is a schematic representation of a lighting device according to an embodiment of the present disclosure.

FIG. 10 is a schematic illustrative representation of a lighting device according to an embodiment of the present disclosure. The lighting device 1400 may include a housing 1401, a light source 1402, a circuit board 1403, an optical filter 1404, and a light diffusing section 1405. The light source 1402 may include the organic EL element according to an embodiment of the present disclosure. The optical filter 1404 may be intended to improve the color rendering properties of the light source 1402. The light diffusion section 1405 diffuses light emitted from the light source 1402 effectively and helps the light reach a wide region for, for example, lighting up. A cover may be provided at an outermost portion.

The region of emission of the lighting device 1400 may be separated from each other. The light-emitting device of the present disclosure is effective in suppressing emission from an undesired region.

The lighting device illuminates, for example, a room. The lighting device may emit light of cool white, sunshine color, or any other color from blue to red. The lighting device may include a dimmer circuit that dims the light. The lighting device may include the organic luminescent element according to an embodiment of the present disclosure and a power supply circuit connected to the organic luminescent element. The power supply circuit converts alternating voltage to direct voltage. White has a color temperature of 4200 K and sunshine color has a color temperature of 5000 K. The lighting device may include a color filter.

The lighting device may include a heat radiation section. The heat radiation section is intended to dissipate heat from the device and may be made of, for example, a metal having a high specific heat or liquid silicon.

Figure 11:
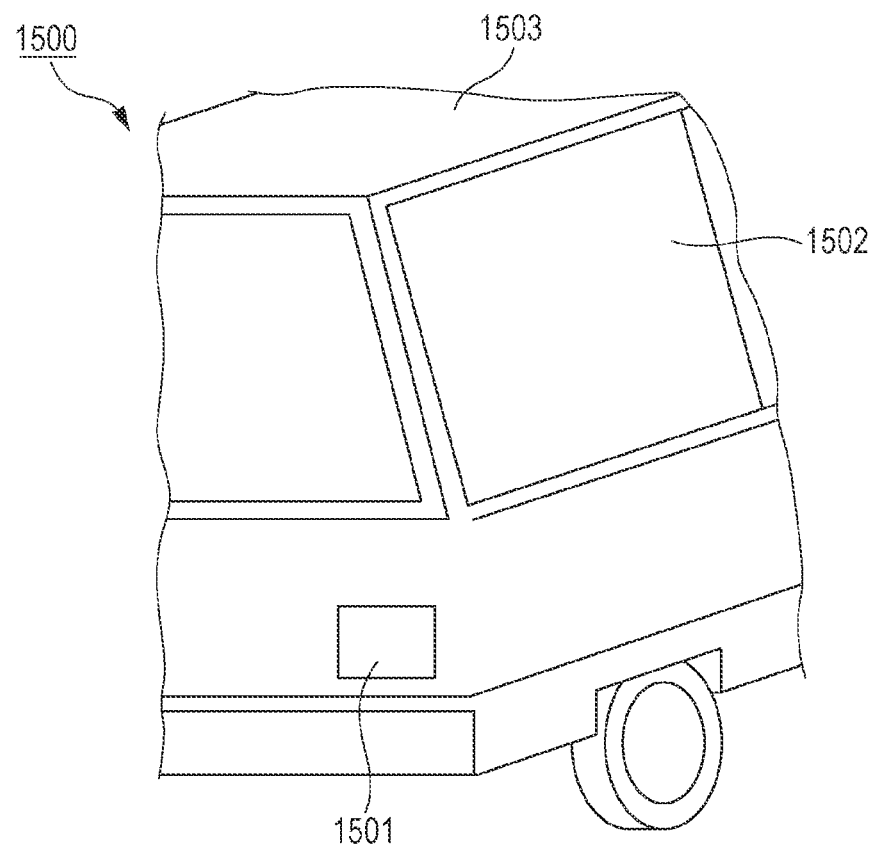
FIG. 11 is a schematic representation of a movable body including a lighting device according to an embodiment of the present disclosure.

FIG. 11 is a schematic view of an automobile that is an implementation of the movable body according to an embodiment of the present disclosure. The automobile 1500 has a tail lamp 1501 that is a type of lighting device, and the tail lamp 1501 may light when the breaks are applied.

The tail lamp 1501 may include the organic luminescent element according to an embodiment of the present disclosure. The tail lamp may include a protective member that protects the organic EL element. The protective member may be made of any material provided that it has a strength to some extent and is transparent. In some embodiments, the protective member may be made of polycarbonate or the like. The polycarbonate may be mixed with a furandicarboxylic acid derivative, an acrylonitrile derivative, or the like.

The automobile 1500 may include a car body 1503 and a window 1502 attached to the car body 1503. The window 1502 may be a transparent display unless it is intended for checking of the front and rear of the automobile. The transparent display may include the organic luminescent element according to an embodiment of the present disclosure. In this instance, the members such as electrodes of the organic luminescent element are made of a transparent material.

In an embodiment, the movable body may be a ship, an aircraft, a drone, or the like. The movable body may include an enclosure and a lighting device provided for the enclosure. The lighting device may emit light to provide a notification of the position of the enclosure. The lighting device includes the organic luminescent element according to an embodiment of the present disclosure.

In an embodiment, the organic luminescent element may be used for displaying an image. In this instance, the emission from the organic luminescent element has a luminance that is controlled by a TFT, or switching element, and a plurality of such organic EL elements are arranged in a plane so that an image is displayed by emission luminances of the organic luminescent elements. The TFT may be substituted by any other switching element, such as a transistor made of a low-temperature polysilicon or an active matrix driver on or in a substrate, such as a silicon substrate. Whether on a substrate or in a substrate depends on definition. For example, for a definition of a QVGA level for 1 inch, the organic EL elements may be disposed on a silicon substrate. The display device including the organic luminescent elements according to the present disclosure is operable to display high-quality images over a long time.

EXAMPLES

Example 1

Light-emitting device D100 was produced by the process described below, and the resulting light-emitting device was examined for leakage between neighboring organic EL elements, the power consumption, and other properties of the device.

As shown in FIG. 1, reflection electrodes 2 were formed on a substrate by patterning, and an insulating layer 3 was formed between the organic EL elements. The insulating layer 3 was a silicon oxide film and had a thickness of 65 nm. The taper angle between the side wall and the substrate was 80° at the aperture for the organic EL elements and 75° at the region between the organic EL elements. The pixels were arranged in a delta array with a distance of 1.4 µm between apertures and a distance of 0.6 µm between the reflection electrodes. The hole injection layer was formed of the following compound 1 to a thickness of 3 nm over the reflection electrodes.

The hole transport layer was formed of exemplified compound HT9 to a thickness of 15 nm, and an electron blocking layer was formed of exemplified compound HT27 to a thickness of 10 nm. A first luminescent layer containing 97% by weight of compound 2 shown below as the host material and 3% by weight of compound 3 shown below as the emission dopant was formed to a thickness of 10 nm. The hole mobilities of exemplified compounds HT9 and HT27 and compound 2 were $2\times10^{-3}$ cm$^2$/(V·s), $5\times10^{-4}$ cm$^2$/(V·s), and $1\times10^{-3}$ cm$^2$/(V·s), respectively.

A second luminescent layer containing 99% by weight of compound 2 as the host material and 1% by weight of compound 4 shown below as the emission dopant was formed.

An electron transport layer was formed of compound 5 shown below to a thickness of 110 nm. An electron injection layer was formed of LiF to a thickness of 0.5 nm. The light extraction electrode was formed of a MgAg alloy to a thickness of 10 nm. The ratio of Mg to Ag was 1:1. Then, SiN was deposited to a thickness of 1.5 µm by CVD to yield a sealing layer.

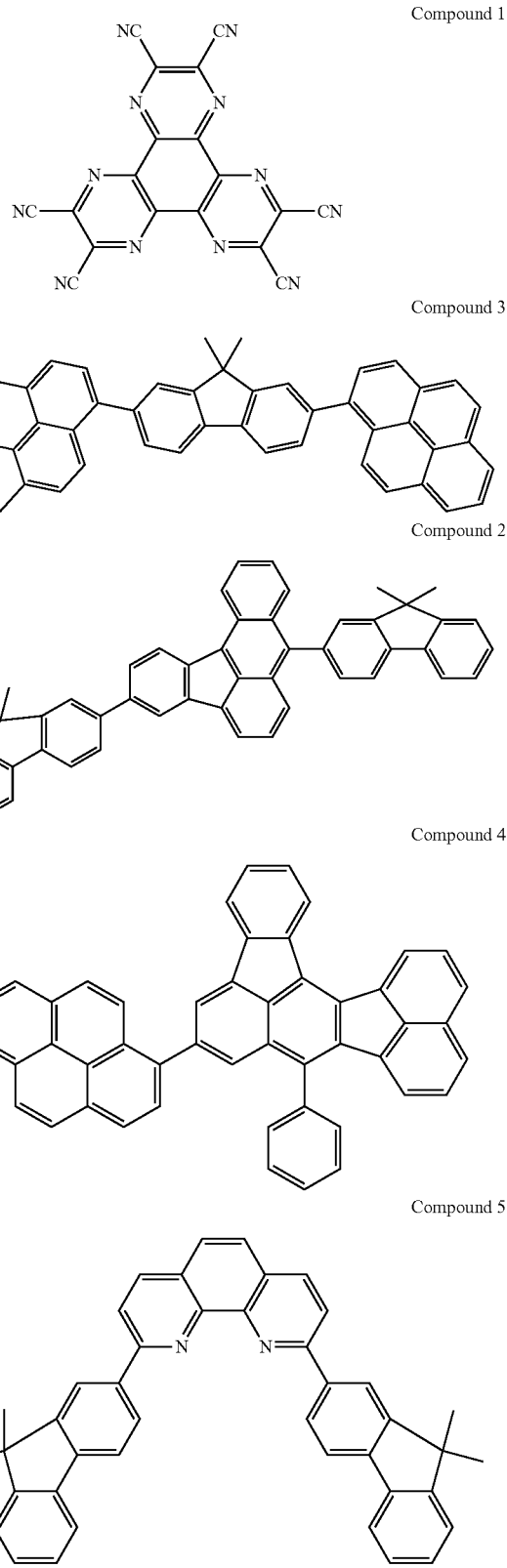

Table 1 shows the specifications used for estimating the power consumption of the display device of the present Example. The organic EL element aperture ratio was 50%, and the R, G, and B organic EL element aperture ratios were each 16.7%. For the estimation of the power consumption, the power required for the display device with the specification shown in Table 1 to emit white light having a color temperature of 6500 K (CIE(x,y)=(0.313, 0.329)) and a luminance of 500 cd/cm$^2$ was calculated. More specifically, the current required for the R, the G, and the B organic EL elements was calculated from the measured luminous efficiency. The power consumption was calculated from the required current value on the assumption that the driving voltage was 10.0 V.

TABLE 1

|  |  | Unit |
| --- | --- | --- |
| Diagonal inch |  | 0.5 | [inch] |
| Vertical proportion |  | 3 |  |
| Lateral proportion |  | 4 |  |
| Sub pixel aperture ratio |  | 16.7 | [%] |
| Pixel aperture ratio |  | 50 | [%] |
| Intended chromaticity | CIE_x | 0.313 |  |
|  | CIE_y | 0.329 |  |
| White light luminance |  | 500 | [cd/m$^2$] |
| Driving voltage (Fixed) |  | 10 | [V] |

The leakage between organic EL elements was estimation by using as an index the $I_{leak}/I_{oled}$ ratio of current $I_{leak}$ flowing between the pixels to current $I_{oled}$ flowing in each organic EL element when current $I_{oled}$ was 0.1 [nA/pixel].

Similarly, light-emitting devices D101 to D108 were produced in the same manner as device D100, except that each layer was formed to the thickness shown in Table 2. Table 2 shows the thicknesses of the layers of light-emitting devices D100 to D108 and measurement results.

compounds in the hole transport layer and the results of hole mobility measurement. By using an intermixed layer as the hole transport layer, the hole mobility can be reduced, and by increasing the proportion of the compound having a low hole mobility, that is, compound HT27, the resistance in the in-plane direction can be dramatically increased.

TABLE 3

| Element |  | Mixing ratio of hole transport layer compound to electron transport layer compound (HT37:HT27) | Hole mobility |
| --- | --- | --- | --- |
| D109 | — | 100:0 | 4.6 × 10$^{-3}$ |
| D110 | Comparative Example | 85:15 | 3.9 × 10$^{-3}$ |
| D111 | Comparative Example | 70:30 | 3.2 × 10$^{-3}$ |
| D112 | Example | 50:50 | 2.3 × 10$^{-3}$ |
| D113 | Example | 25:75 | 1.2 × 10$^{-3}$ |
| D114 | Example | 15:85 | 4.6 × 10$^{-4}$ |

FIG. 4 is a plot of the relationship between the hole mobility and the $I_{leak}/I_{oled}$ ratio of leakage between pixels. Since the thicknesses of the devices shown in Table 3 are the same, the power consumptions of the devices depending on optical interference are the same. FIG. 4 shows that as the hole mobility of the hole transport layer is increased, the ratio of leakage between pixels increases. In particular, when the hole mobility exceeds 2.5×10$^{-3}$ cm$^2$/(V·s), the gradient increases.

These results suggest that the beneficial hole mobility is 2.5×10$^{-3}$ cm$^2$/(V·s) or less. If the hole mobility of the hole transport layer is as low as that of device D114, the thickness

TABLE 2

| Element |  | Hole injection layer [nm] | Hole transport layer [nm] | Electron blocking layer [nm] | First luminescent layer [nm] | $I_{leak}/I_{oled}$ |  | Power consumption [mW] |  |
| --- | --- | --- | --- | --- | --- | --- | --- | --- | --- |
| D100 | Comparative Example | 3 | 15 | 10 | 10 | 0.55 | Bad | 357 | Good |
| D101 | Comparative Example | 3 | 10 | 10 | 10 | 0.42 | Bad | 409 | Bad |
| D102 | Comparative Example | 3 | 5 | 10 | 10 | 0.21 | Good | 488 | Bad |
| D103 | Comparative Example | 3 | 15 | 10 | 15 | 0.61 | Bad | 324 | Good |
| D104 | Comparative Example | 3 | 10 | 10 | 15 | 0.48 | Bad | 363 | Good |
| D105 | Comparative Example | 3 | 5 | 10 | 15 | 0.24 | Good | 422 | Bad |
| D106 | Comparative Example | 3 | 15 | 10 | 20 | 0.67 | Bad | 313 | Good |
| D107 | Comparative Example | 3 | 10 | 10 | 20 | 0.56 | Bad | 332 | Good |
| D108 | Example | 3 | 5 | 10 | 20 | 0.26 | Good | 376 | Good |

The devices exhibiting an $I_{leak}/I_{oled}$ ratio of 0.35 or less were determined to be good, and the devices exhibiting an $I_{leak}/I_{oled}$ ratio of more than 0.35 were determined to be bad. For power consumption, the devices of 400 mW or less were determined to be good, and the devices of more than 400 mW were determined to be bad.

Example 2

Light-emitting devices D109 to D114 used in the present Example were the same as device D108 except that the hole transport layer was an intermixed layer of exemplified compounds HT37 and HT27. Table 3 shows the ratio of the of the hole transport region may be increased. However, an excessively low mobility leads to an increased driving voltage. This should be considered for increasing the thickness. The thickness of the hole transport layer may be 10 nm or less.

Example 3

In the present Example, device D112 was compared with devices D115 and D116. As shown in Table 4, devices D115 and D116 have the same structure as device D112 except for the structure of the hole transport layer.

It is known that an energy barrier is reduced to reduce hole accumulation by providing an intermixed layer of the hole transport layer and the electron blocking layer between the hole transport layer and the electron blocking layer.

A decrease of hole accumulation may cause a decrease in resistance in the in-plane direction. Accordingly, the effect of the intermixed layer was examined by comparing devices D115 and D116 with device D112. Device D115 was produced in the same manner as device D112 except that a hole transport layer containing a hole transporting material HT37 was formed to a thickness of 5 nm and then an intermixed layer of HT37 and HT27 in a ratio of 50:50 was formed to a thickness of 5 nm. Also, device D116 was produced in the same manner as device D112 except that a hole transport layer containing a hole transporting material HT37 was formed to a thickness of 5 nm, but an intermixed layer was not formed.

TABLE 4

| | | Thickness [nm] | | Rate of leakage $I_{leak}/I_{oled}$ | |
|---|---|---|---|---|---|
| | | Hole transport layer | Intermixed hole transport layer | Electron blocking layer | |
| D112 | Example | 0 | 5 | 10 | 0.24 Good |
| D115 | Comparative Example | 5 | 5 | 10 | 1.81 Bad |
| D116 | Comparative Example | 5 | 0 | 10 | 1.32 Bad |

As shown in Table 4, in device D116 using H37 having a high hole mobility, the ratio of leakage between pixels was as high as 1.32. For device D115 provided with an intermixed layer between the hole transport layer and the electron blocking layer, the ratio of leakage between pixels was 1.81.

These results suggest that the resistance to leakage between pixels does not depend on whether hole accumulation is reduced by the presence of an intermixed layer, but depends mainly on the total thickness of the hole transport layer and the electron blocking layer.

Figure 5:
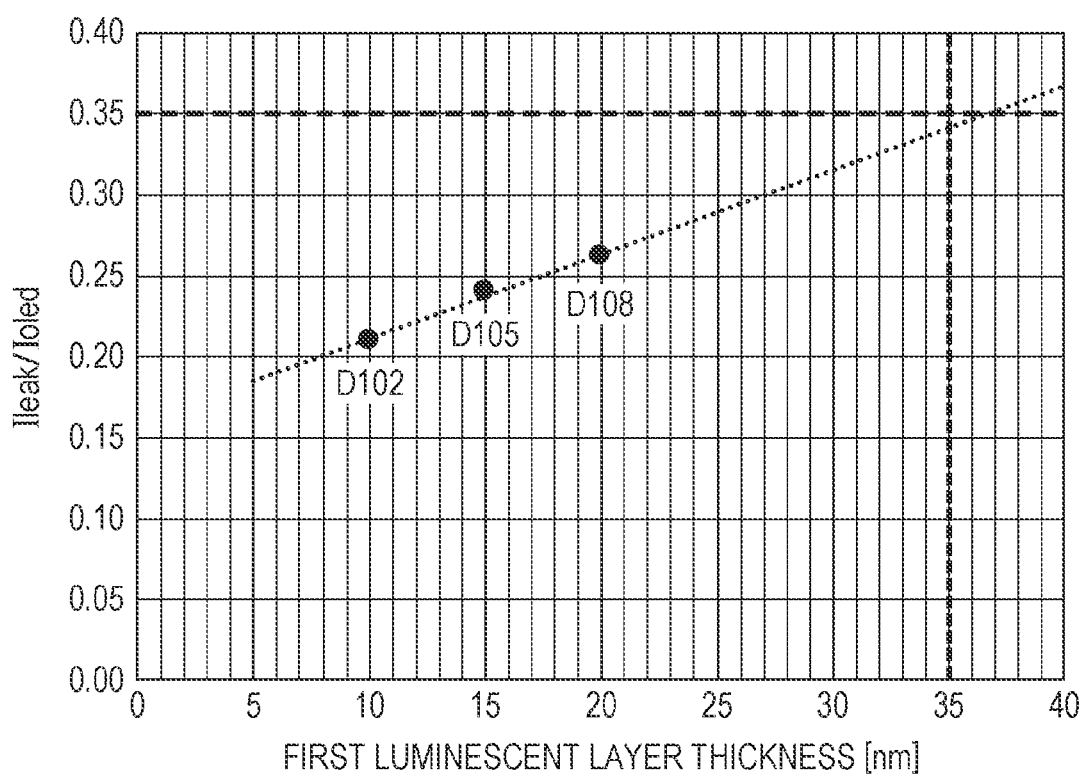
FIG. 5 is a plot showing the relationship between the thickness of the first luminescent layer and the $I_{leak}/I_{oled}$ ratio of the leakage current $I_{leak}$ flowing from a target organic EL element to an adjacent organic EL element to the current $I_{oled}$ flowing into the target organic EL element.

FIG. 5 is a plot showing the relationship between the thickness of the first luminescent layer and the ($I_{leak}/I_{oled}$) ratio of the leakage current $I_{leak}$ flowing from a target organic EL element to an adjacent organic EL element to the current $I_{oled}$ flowing into the target organic EL element. The threshold of the thickness of the first luminescent layer at which the $I_{leak}/I_{oled}$ ratio is 0.35 or less is estimated to be 35 nm or less based on the above examination about leakage current.

As described above, the present disclosure provides a light-emitting device including organic EL elements in which leakage current between neighboring organic EL elements is reduced, and having a low power consumption reduced by using optical interference.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

What is claimed is:
1. A light-emitting device comprising:
a reflection electrode;
a hole transport region;
a first luminescent layer being of an electron trapping type; and
a light extraction electrode, in this order,
wherein the hole transport region of the light-emitting device and a hole transport layer of another light-emitting device are disposed continuously;
wherein the first luminescent layer includes a first surface and a second surface closer to the light extraction electrode than the first surface, and
wherein a distance between the reflection electrode and the second surface of the first luminescent layer is equivalent to a length enabling emission from the first luminescent layer to be enhanced.

2. The light-emitting device according to claim 1, wherein the hole transport region includes a hole transport layer and an electron blocking layer.

3. The light-emitting device according to claim 2, wherein the hole transport layer contains a first compound and a second compound, and the electron blocking layer contains the first compound.

4. The light-emitting device according to claim 1, wherein the hole transport layer contains a first compound and a second compound whose HOMO is higher than HOMO of the first compound.

5. The light-emitting device according to claim 4, wherein a weight ratio of the first compound with respect to the total weight of the first compound and the second compound is equal to or more than that of the second compound.

6. The light-emitting device according to claim 5, wherein the weight ratio of the first compound is range from 50% to 95%.

7. The light-emitting device according to claim 1, further including a second luminescent layer between the first luminescent layer and the light extraction electrode.

8. The light-emitting device according to claim 1, wherein a hole transport layer of the hole transport region includes one of compounds represented by general formulas [1] and [2]:

[1]

wherein $Ar_1$ to $Ar_3$ each represent one independently selected from the group consisting of substituted or unsubstituted aryl groups selected from the group consisting of phenyl, bisphenyl, terphenyl, fluorenyl, naphthyl, and spirofluorenyl and substituted or unsubstituted heterocyclic groups selected from the group consisting of dibenzofuranyl, dibenzothiophenyl, thiophenyl, furanyl, and carbazolyl; and

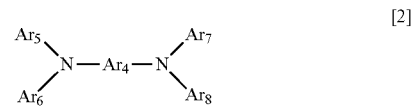

[2]

wherein $Ar_4$ represents a substituted or unsubstituted aryl group selected from the group consisting of phenyl, biphenyl, terphenyl, fluorenyl, dibenzofuranyl, dibenzothiophenyl, and naphthyl, and $Ar_5$ to $Ar_8$ each represent one independently selected from the group consisting of substituted or unsubstituted aryl groups consisting of phenyl, biphenyl, terphenyl, fluorenyl, phenanthrenyl, and pyrenyl; and substituted or unsubstituted heterocyclic groups including dibenzofuranyl, dibenzothiophenyl, thiophenyl, furanyl, and carbazolyl.

9. The light-emitting device according to claim 8, wherein the hole transport layer contains at least two compounds selected from the compounds represented by the general formulas [1] and [2].

10. The light-emitting device according to claim 1, wherein the light-emitting device further includes a hole injection layer disposed between the reflection electrode and the first luminescent layer, the hole injection layer containing a compound having an electron affinity of 5.0 eV or more.

11. The light-emitting device according to claim 1, wherein a hole transport layer of the hole transport region has a thickness of 5 nm or less.

12. The light-emitting device according to claim 1, the light-emitting device further includes a second luminescent layer between the first luminescent layer and the light extraction electrode, the first luminescent layer being operable to emit light other than blue light, the second luminescent layer being operable to emit blue light.

13. A display device comprising:
the light-emitting device as set forth in claim 1; and
an active element connected to the light-emitting device.

14. An imaging apparatus comprising:
an optical system including a plurality of lenses;
an imaging element capable of receiving light that has passed through the optical system; and
a display section on which information obtained by the imaging element is displayed, the display section including the light-emitting device as set forth in claim 1.

15. A movable body comprising:
an enclosure; and
a lighting device provided for the enclosure, the lighting device including the light-emitting device as set forth in claim 1.

* * * * *